US011904005B2

(12) United States Patent
Barta et al.

(10) Patent No.: US 11,904,005 B2
(45) Date of Patent: Feb. 20, 2024

(54) **COMPOSITIONS AND METHODS OF ENHANCING IMMUNE RESPONSES TO *EIMERIA* OR LIMITING *EIMERIA* INFECTION**

(71) Applicants: THE BOARD OF TRUSTEES OF THE UNIVERSITY OF ARKANSAS, Little Rock, AR (US); THE TEXAS A&M UNIVERSITY SYSTEM, College Station, TX (US)

(72) Inventors: John R. Barta, Guelph (CA); Luc Berghman, College Station, TX (US); Srichaitanya Shivaramaiah, Bangalore (IN); Olivia B. Faulkner, Farmington, AR (US); Lisa Bielke, Wooster, OH (US); Billy Hargis, Fayetteville, AR (US)

(73) Assignees: The Board of Trustees of the University of Arkansas, Little Rock, AR (US); The Texas A&M University System, College Station, TX (US)

( * ) Notice: Subject to any disclaimer, the term of this patent is extended or adjusted under 35 U.S.C. 154(b) by 0 days.

(21) Appl. No.: 17/824,378

(22) Filed: May 25, 2022

(65) Prior Publication Data

US 2022/0288175 A1 Sep. 15, 2022

Related U.S. Application Data

(62) Division of application No. 17/023,795, filed on Sep. 17, 2020, now Pat. No. 11,364,290, which is a division of application No. 16/439,511, filed on Jun. 12, 2019, now Pat. No. 10,792,351, which is a division of application No. 15/877,598, filed on Jan. 23, 2018, now Pat. No. 10,328,137, which is a division of application No. 15/450,138, filed on Mar. 6, 2017, now Pat. No. 9,884,099, which is a division of application No. 14/768,011, filed as application No. PCT/US2014/016359 on Feb. 14, 2014, now Pat. No. 9,603,915.

(60) Provisional application No. 61/764,681, filed on Feb. 14, 2013.

(51) Int. Cl.

| | |
|---|---|
| ***A61K 39/40*** | (2006.01) |
| ***A61K 39/002*** | (2006.01) |
| ***C07K 14/445*** | (2006.01) |
| ***A61K 39/012*** | (2006.01) |
| ***A61K 39/015*** | (2006.01) |
| *A61K 39/00* | (2006.01) |

(52) U.S. Cl.

CPC .......... *A61K 39/002* (2013.01); *A61K 39/012* (2013.01); *A61K 39/015* (2013.01); *C07K 14/445* (2013.01); *A61K 2039/523* (2013.01); *A61K 2039/53* (2013.01); *A61K 2039/542* (2013.01); *A61K 2039/55* (2013.01); *A61K 2039/552* (2013.01); *A61K 2039/55583* (2013.01)

(58) Field of Classification Search

None

See application file for complete search history.

(56) References Cited

U.S. PATENT DOCUMENTS

| | | | |
|---|---|---|---|
| 5,540,926 | A | 7/1996 | Aruffo et al. |
| 5,565,321 | A | 10/1996 | Spriggs et al. |
| 5,683,700 | A | 11/1997 | Charles et al. |
| 5,716,805 | A | 2/1998 | Srinivasan et al. |
| 5,747,309 | A | 5/1998 | Allan et al. |
| 5,817,516 | A | 10/1998 | Kehry et al. |
| 5,961,974 | A | 10/1999 | Armitage et al. |
| 5,962,406 | A | 10/1999 | Armitage et al. |
| 5,981,724 | A | 11/1999 | Armitage et al. |
| 6,087,329 | A | 7/2000 | Armitage et al. |
| 6,190,669 | B1 | 2/2001 | Noriega et al. |
| 6,264,951 | B1 | 7/2001 | Armitage et al. |
| 6,306,387 | B1 | 10/2001 | Galan |
| 6,410,711 | B1 | 6/2002 | Armitage et al. |
| 6,479,258 | B1 | 11/2002 | Short |
| 6,713,279 | B1 | 3/2004 | Short |
| 6,902,906 | B1 | 6/2005 | Chatfield |
| 6,923,957 | B2 | 8/2005 | Lowery et al. |
| 6,923,958 | B2 | 8/2005 | Xiang et al. |
| 6,936,425 | B1 | 8/2005 | Hensel et al. |
| 6,969,609 | B1 | 11/2005 | Schlom et al. |
| 7,087,573 | B1 | 8/2006 | Lazarus et al. |

(Continued)

FOREIGN PATENT DOCUMENTS

| | | |
|---|---|---|
| CN | 101234196 | 8/2008 |
| WO | 1993008207 | 4/1993 |

(Continued)

OTHER PUBLICATIONS

International Search Report and Written Opinion of the International Searching Authority for Application No. PCT/US11/22062 dated Mar. 29, 2011 (11 pages).

(Continued)

*Primary Examiner* — Jennifer E Graser

(74) *Attorney, Agent, or Firm* — QUARLES & BRADY LLP

(57) ABSTRACT

Vaccine vectors and methods of using the vaccine vectors to enhance the immune response to an Apicomplexan parasite and reduce the morbidity or mortality associated with subsequent infection are provided herein. The vaccine vectors include a polynucleotide encoding a Rhomboid polypeptide and optionally include an immune-stimulatory polypeptide suitably expressed on the surface of the vaccine vector.

20 Claims, 5 Drawing Sheets

Specification includes a Sequence Listing.

(56) References Cited

U.S. PATENT DOCUMENTS

| | | | |
|---|---|---|---|
| 7,118,751 | B1 | 10/2006 | Ledbetter et al. |
| 7,238,499 | B2 | 7/2007 | Reddy |
| 7,332,298 | B2 | 2/2008 | Kornbluth |
| 7,371,392 | B2 | 5/2008 | Tripp et al. |
| 7,405,270 | B2 | 7/2008 | Armitage et al. |
| 7,423,137 | B2 | 9/2008 | Belli et al. |
| 7,462,707 | B1 | 12/2008 | Witcombe et al. |
| 7,495,090 | B2 | 2/2009 | Prussak et al. |
| 7,803,765 | B2 | 9/2010 | Watt et al. |
| 7,842,501 | B2 | 11/2010 | Cai et al. |
| 7,928,213 | B2 | 4/2011 | Prussak et al. |
| 7,968,695 | B2 | 6/2011 | Belli et al. |
| 8,142,771 | B2 | 3/2012 | Suo et al. |
| 8,604,178 | B2 | 12/2013 | Bottje et al. |
| 8,906,634 | B2 | 12/2014 | Gougeon et al. |
| 8,956,618 | B2 | 2/2015 | Berghman et al. |
| 8,956,849 | B2 | 2/2015 | Bottje et al. |
| 8,961,990 | B2 | 2/2015 | Hargis et al. |
| 9,125,854 | B2 | 9/2015 | Bottje et al. |
| 9,226,957 | B2 | 1/2016 | Bottje et al. |
| 9,603,915 | B2 | 3/2017 | Barta et al. |
| 9,913,893 | B2 | 3/2018 | Berghman |
| 10,004,798 | B2 | 6/2018 | Bottje |
| 10,016,493 | B2 | 7/2018 | Bottje |
| 2001/0021386 | A1 | 9/2001 | Nuijten et al. |
| 2003/0045492 | A1 | 3/2003 | Tang et al. |
| 2003/0091548 | A1 | 5/2003 | Young |
| 2003/0165538 | A1 | 9/2003 | Goldman et al. |
| 2004/0006006 | A9 | 1/2004 | Armitage et al. |
| 2004/0047873 | A1 | 3/2004 | Al-Shamkhani et al. |
| 2004/0053841 | A1 | 3/2004 | Tracey |
| 2004/0141948 | A1 | 7/2004 | O'Keefe |
| 2004/0156851 | A1 | 8/2004 | Newman |
| 2004/0203039 | A1 | 10/2004 | Hensel et al. |
| 2004/0242481 | A1 | 12/2004 | Bianchi |
| 2005/0033042 | A1 | 2/2005 | Belli |
| 2005/0181994 | A1 | 8/2005 | Chamberlain et al. |
| 2005/0226888 | A1 | 10/2005 | Deisseroth et al. |
| 2006/0014248 | A1 | 1/2006 | Marshall et al. |
| 2006/0078994 | A1 | 4/2006 | Healey et al. |
| 2006/0121047 | A1 | 6/2006 | Tracey |
| 2006/0233829 | A1 | 10/2006 | Curtiss, III |
| 2006/0286074 | A1 | 12/2006 | Tang et al. |
| 2007/0025982 | A1 | 2/2007 | Ledbetter et al. |
| 2007/0082400 | A1 | 4/2007 | Healey et al. |
| 2007/0128223 | A1 | 6/2007 | Tang et al. |
| 2007/0237779 | A1 | 10/2007 | Ledbetter et al. |
| 2008/0004207 | A1 | 1/2008 | Tsung et al. |
| 2008/0075728 | A1 | 3/2008 | Newman |
| 2008/0124320 | A1 | 5/2008 | O'Keefe |
| 2008/0305120 | A1 | 12/2008 | Messmer et al. |
| 2009/0004194 | A1 | 1/2009 | Kedl |
| 2009/0196888 | A1 | 8/2009 | Belli |
| 2010/0040608 | A1 | 2/2010 | Wahren-Herlenius et al. |
| 2010/0047231 | A1 | 2/2010 | Zabaleta Azpiroz et al. |
| 2010/0112002 | A1 | 5/2010 | Lien et al. |
| 2010/0150958 | A1 | 6/2010 | Sheppard |
| 2010/0233152 | A1 | 9/2010 | Bullerdiek |
| 2010/0291109 | A1 | 11/2010 | Kedl |
| 2010/0292309 | A1 | 11/2010 | Vile et al. |
| 2011/0020318 | A1 | 1/2011 | Tracey et al. |
| 2011/0111015 | A1 | 5/2011 | Bottje |
| 2012/0282291 | A1 | 11/2012 | Berghman |
| 2015/0150958 | A1 | 6/2015 | Pillich et al. |
| 2015/0297714 | A1 | 10/2015 | Hargis |
| 2016/0000895 | A1 | 1/2016 | Barta |
| 2017/0143823 | A1 | 5/2017 | Hargis |
| 2018/0333474 | A1 | 11/2018 | Bottje |

FOREIGN PATENT DOCUMENTS

| | | |
|---|---|---|
| WO | 1995014487 | 6/1995 |
| WO | 1996026735 | 9/1996 |
| WO | 1996040918 | 12/1996 |
| WO | 1999027948 | 6/1999 |
| WO | 1999032138 | 7/1999 |
| WO | 1999059609 | 11/1999 |
| WO | 2000063395 | 10/2000 |
| WO | 2000063405 | 10/2000 |
| WO | 2001042298 | 6/2001 |
| WO | 2001056602 | 8/2001 |
| WO | 2002036769 | 5/2002 |
| WO | 2002092004 | 11/2002 |
| WO | 2002092773 | 11/2002 |
| WO | 2003004684 | 1/2003 |
| WO | 2003026691 | 4/2003 |
| WO | 2003099340 | 12/2003 |
| WO | 2004009615 | 1/2004 |
| WO | 2004046338 | 6/2004 |
| WO | 2004046345 | 6/2004 |
| WO | 2005025604 | 3/2005 |
| WO | 2005035570 | 4/2005 |
| WO | 2005058950 | 6/2005 |
| WO | 2005113598 | 12/2005 |
| WO | 2006012373 | 2/2006 |
| WO | 2006042177 | 4/2006 |
| WO | 2006105972 | 10/2006 |
| WO | 2007011606 | 1/2007 |
| WO | 2007042583 | 4/2007 |
| WO | 2007054658 | 5/2007 |
| WO | 2007056266 | 5/2007 |
| WO | 2007103048 | 9/2007 |
| WO | 2007117682 | 10/2007 |
| WO | 2008109825 | 9/2008 |
| WO | 2009059298 | 5/2009 |
| WO | 2010056709 | 5/2010 |
| WO | 2011091255 | 7/2011 |

OTHER PUBLICATIONS

Jenkins, M.C., "Progress on developing a recombinant coccidiosis vaccine," International Journal of Parasitology (1998) 28:1111-1119.

Kimura, R. et al., "Enhancement of antibody response by high mobility group box protein-1-based DNA immunization," J. of Immunol. Methods (2010) 361:21-30.

Koch, F. et al., "High level IL-12 production by murine dendritic cells: upregulation via MHC class II and CD40 molecules and downregulation by IL-4 and IL-10," J. Exp. Med. (1996) 184:741-746.

Konjufca, V. et al., "A recombinant attenuated *Salmonella enterica* serovar *typhimurium* vaccine encoding *Eimeria acervulina* antigen offers protection against *E. acervulina* challenge," Infection and Immunity (2006) 74:6785-6796.

Kotton, C.N. et al., "Enteric pathogens as vaccine vectors for foreign antigen delivery," Infect. Immun. (2004) 72:5535-5547.

Kwon, Y.M. et al., "*Salmonella*-based vaccines for infectious diseases," Expert Review of Vaccines (2007) 6(2):147-152.

Lavelle, E.C. et al., "Delivery systems and adjuvants for oral vaccines," Expert Opin. Drug Deliv. (2006) 3(6):747-762.

Layton et al., Evaluation of *Salmonella*-vectored Campylobacter peptide epitopes for reduction of Campylobacter iejuni in broiler chickens, Clin. Vaccine Immunol. (2011) 18(3):449-454.

Layton, S.L., et al., "Vaccination of chickens with recombinant *Salmonella* expressing M2e and CD154 epitopes increases protection and decreases viral shedding after low pathogenic avian influenza challenge," Poultry Science (2009) 88(11):2244-2252.

Lee, J.S. et al., "Surface-displayed viral antigens on *Salmonella* carrier vaccine," Nat. Biotechnol. (2000) 18:645-648.

Li, J, et.al., (2006). *Eimeria tenella*: Cloning of a new *Eimeria tenella* cDNA encoding a protein related to rhomboid family from F2 hybrid strain. Experimental Parasitology:113(215-20).

Li, J. et al. Efficacy of *Eimeria tenella* rhomboid-like rotein as a subunit vaccine in proterctive immunity against homologous challenge. Parasitol. Res. 2012. vol. 110, Issue 3, 1139-1145.

Li, J. et al., "Toxoplasma gondii rhomboid protein 1 (TgROM1) is a potential vaccine candidate against toxoplasmosis," Veterinary parasitology (2012), 184(2):154-160.

(56) References Cited

OTHER PUBLICATIONS

Li, W., "Synergistic antibody induction by antigen-CD40 ligand fusion protein as improved immunogen," Immunology (2005) 115(2):215-222.
Liu, Y et al., "Protective immunity induced by a DNA vaccine encoding rhomboid against homologous challenge," Parasitology Research (2012) 112(1):251-257.
Lowe, D.C. et al., "Characterization of candidate live oral *Salmonella typhi* vaccine strains harboring defined mutations in aroA, aroC, and htrA," Infection and Immunity Feb. 1999:700-707.
Mann, J.F. et al., "Delivery systems: a vaccine strategy for overcoming mucosal tolerance?" Expert Rev. Vaccines (2009) 8(1):103-112.
Manoj, S. et al., "Targeting with Bovine CD154 enhances humoral immune responses induced by a DNA vaccine in sheep," (2003) Journal of Immunology 170:989-996.
Mauriello, E.M.F. et al., "Display of heterologous antigens on the Bacillus subtilis spore coat using CotC as a fusion partner," (2004) Vaccine 22(9-10):1177-1187.
Mendoza, R.B. et al., "Cutting edge: Immunostimulatory effects of a plasmid expressing CD40 ligand (CD154) on gene immunization," Journal of Immunology (1997) 159(12):5777-5781.
Miga, A. et al., "The role of CD40-CD154 interactions in the regulation of cell mediated immunity," Immunol. Invest. (2000) 29:111-114.
Mikayama, et al., "Molecular cloning and functional expression of a cDNA encoding glycosylation-inhibiting factor," (1993) PNAS 90:10056-10060.
Mogensen, T.H., "Pathogen recognition and inflammatory signaling in innate immune defenses," Clin. Microbiol. Rev. (2009) 22(2):240-273.
Mohamadzadeh, M. et al., "Targeting mucosal dendritic cells with microbial antigens from probiotic lactic acid bacteria," Expert Rev. Vaccines (2008) 7(2):163-174.
Moyle, P.M. et al., "Mucosal immunisation: adjuvants and delivery systems," Curr. Drug Deliv. (2004) 1(4):385-396.
Muthumani, G. et al., "Co-immunization with an optimized plasmid-encoded immune stimulatory interleukin, high-mobility group box 1 protein, results in enhanced interferon-γ secretion by antigen-specific CD8 T cells," Immunology (2009) 128: e612-e620.
Nakajima, A. et al., "Antitumor effect of CD40 ligand: Elicitation of local and systemic antitumor responses by IL-12 and B7," (1998) Journal of Immunology 161:1901-1907.
National Center for Biotechnology Information [http://www.ncbi.nlm.nih.gov/protein/74811618?].
Notice of Allowance for U.S. Appl. No. 15/450,138 dated Jun. 19, 2017.
O'Callaghan, D. et al., "Immunogenicity of foreign peptide epitopes expressed in bacterial envelope proteins," Research in Microbiology (1990) 141:963-969.
Ochoa-Reparaz, J. et al., "Humoral immune reponse in hens naturally infected with *Salmonella enteritidis* against puter membrane proteins and other surface structural antigens," (2004) Vet. Res. 35:291-298.
Office Action for U.S. Appl. No. 14/623,050 dated Dec. 15, 2016.
Office Action for U.S. Appl. No. 14/623,050 dated Jun. 28, 2016.
Office Action for U.S. Appl. No. 12/740,608 dated Aug. 22, 2013 (24 pages).
Office Action for U.S. Appl. No. 14/768,011 dated Jun. 1, 2016 (39 pages).
Office Action for U.S. Appl. No. 15/877,598 dated Jul. 31, 2018 (38 pages).
Office Action for U.S. Appl. No. 16/439,511 dated Oct. 24, 2019 (19 pages).
Office Action of U.S. Appl. No. 12/740,608 dated Jun. 16, 2014 (10 pages).
Opitz, C, et.al., Intramembrane cleavage of microneme proteins at the surface of the apicomplexan parasite *Toxoplasma gondii*. 2002 The EMBO Journal:7(1577-85).
Pasetti, M. et al., "Animal models paving the way for clinical trials of attenuated *Salmonella enterica* servoar *typhi* ive oral vaccines and live vectors," Vaccine (2003) 21:401-418.
Patarroyo, M. et al., "Induction of protective immunity against experimental infection with malaria using synthetic peptides," (1987) Nature 328(6131):629-632.
Pisetsky, D.S. et al., "High-mobility group box protein 1 (HMGB1): an alarmin mediating the pathogenesis of rheumatic disease," Arthritis Res. Ther. (2008) 10(3):209.
Pogonka, T. et al., "A single dose of recombinant *Salmonella* typhimurium induces specific humoral immune responses against heterologous *Eimeria tenella* antigens in chicken," International Journal of Parasitology (2003) 33:81-88.
Rabsch, W. et al., "Competitive exclusion of *Salmonella enteritidis* by *Salmonella gallinarum* in poultry," Emerging Inf. Diseases (2000) 6(5):443-448.
Restriction Requirement for U.S. Appl. No. 14/768,011 dated Mar. 7, 2016 (6 pages).
Restriction Requirement for U.S. Appl. No. 15/877,598 dated Apr. 20, 2018.
Rovere-Querini, P. et al., "HMGB1 is an endogenous immune adjuvant released by necrotic cells," EMBO Rep. (2004) 5(8):825-830.
Rudinger, et al., Characteristics of the amino acids as components of a peptide hormone sequence (1976) Peptide Hormones Biol. Council 5-7.
Russmann, H. et al., "Delivery of epitopes by the *Salmonella* type III secretion system for vaccine development," Science (1998) 281(5376):565-568.
Agterberg, M. et al., "Outer membrane protein PhoE as a carrier for the exposure of foreign antigenic determinants at the bacterial cell surface," Antonie Van Leeuwenhoek (1991) 59(4):249-262.
Al-Ramadi, B. K. et al., "CD154 is essential for Protective Immunity in Experimental *Salmonella* Infection: Evidence for a Dual Role in Innate and Adaptive Immune Responses" J Immunol (2006) 176: 496-506.
Al-Ramadi, B. K. et al., "Induction of innate immunity by IL-2 expressing *Salmonella* confers protection against letal challenge," Mol. Immunol. (2003) 39:763-770.
Al-Ramadi, B. K. et al., "Influence of vector-encoded cytokines on anti-*Salmonella* immunity: divergent effects of interleukin-2 and tumor necrosis factor alpha," Infect. Immun. (2001) 69:3960-3988.
Andersson, U. et al., "HMGB1 is a therapeutic target for sterile inflammation and infection," Annu. Rev. Immunol. (2011) 29:139-162.
Babu, U., et al., "*Salmonella enteritidis* clearance and immune responses in chickens following *Salmonella* vaccination and challenge," Vet. Immunol. Immunopathol. (2004)101:251-257.
Barr, T.A. et al., "A potent adjuvant effect of CD40 antibody attached to antigen," Immunology (2003) 109:87-92.
Barrow, P. A., et al., "Reduction in faecal excretion of *Salmonella typhimurium* strain F98 in chickens vaccinated with live and killed *S. typhimurium* organisms," Epidemiol. Infect. (1990) 104:413-426.
Blomfield, I.C. et al., "Allelic exchange in *Escherichia coli* using the Bacillus subtilis sacB gene and a temperature-sensitive pSC101 replicon," Mol Microbiol (1991) 5(6):1447-1457.
Brossier, F. et al., "A spatially localized rhomboid protease cleaves cell surface adhesins essential for invasion by Toxoplasma," Proceedings of the National Academy of Sciences (2005) 102(11):4146-4151.
Buckley, A.M. et al., "Evaluation of live-attenuated *Salmonella* vaccines expressing Campylobacter antigens for control of *C. jejuni* in poultry," (2010) Vaccine 28(4):1094-1105.
Buguliskis, J.S., et.al. Rhomboid 4 (ROM4) affects the processing adhesions and facilitates host cell invasion by Toxoplasma gondii. 2010 PLoS Pathgens:6(4), (1-14).
Charbit, A. et al., "Probing the topology of a bacterial membrane protein by genetic insertion of a foreign epitope; expression at the cell surface," EMBO J (1986) 5(11):3029-3037.
Charbit, A. et al., "Versatility of a vector for expressing foreign polypeptides at the surface of gram-negative bacteria," Gene (1988) 70(1):181-189.

(56) References Cited

OTHER PUBLICATIONS

Chatfield et al., "The development of oral vaccines based on live attenuated *Salmonella* strains," FEMS Immunol. Med. Microbiol. (1993) 7:1-7.
Chothia, C. et al., "The relation between the divergence of sequence and structure in proteins," The EMBO Journal (1986) 5(4):823-826.
Cole, K. et al., ""Evaluation of a novel recombinant *Salmonella* vaccine vector for avian influenza,"" Poultry Science (2007) 86(Supp. 1):585-586.
Cox, M.M. et al., "Scarless and site-directed mutagenesis in *Salmonella enteritidis* chromosome," BMC Biotech. (2007) 7(59):10 pages.
Crawford, J. et al., "Baculovirus-derived hemagglutinin vaccines protect against lethal influenza infections by avian H5 and H7 subtypes," Vaccine (1999) 17:2265-2274.
Danforth, H.D. et al., "Genetically engineered antigen confers partial protection against avian coccidial parasites," (1989) Poultry Science 68:1643-1652.
Dowse, T & Soldati, D. Host cell invasion by the apicomplexans: the significance of microneme protein proteolysis. 2004 Curr. Opinion in Microbiology:7(388-96).
Dowse, T, et.al. Role of proteases during invasion and egress by Plasmodium and Toxoplasma. 2008 Sub-cellular biochemistry:47(121-39).
Du, A. et al., "Efficacy of a DNA vaccine delivered in attenuated *Salmonella typhimurium* against *Eimeria tenella* Infection in chickens," International Journal of Parasitology (2005) 35:777-785.
Duc, L.H. et al., "Bacterial Spores as Vaccine Vehicles," Infection and Immunity (2003) 71(5): 2810-2818.
Dumitriu, I.E et al., "HMGB1: guiding immunity from within," Trends Immunol. (2005) 26(7):381-387.
Ellis, R.W., "New technologies for making vaccines, " (1988) Vaccines, Chapter 29:568-574.
Extended European Search Report for European Patent Application No. 14751914.4 dated Aug. 23, 2016.
Faham, A. et al., "Liposomal Ag engrafted with peptides of sequence derived from HMGB1 induce potent Ag-specific and anti-tumour immunity," Vaccine (2009) 27(42):5846-5854.
Farnell, M.B. et al., "Upregulation of oxidative burst and degranulation in chicken heterophils stimulated with probiotic bacteria," Poult. Sci. (2006) 85:1900-1906.
Fecteau, J.F. et al., "CD40 Stimulation of Human Peripheral B Lymphocytes: Distinct Response from Naïve and Memory Cells," J Immunol (2003) 171:4621-4629.
Fernandez-Cabezudo et al., "Evidence for the requirement for CD40-CD154 interactions in resistance to Infections with attenuated *Salmonella,*" J. Endotoxin Res. (2005) 11:395-399.
Gares, S.L. et al., "Immunotargeting with CD154 (CD40 ligand) enhances DNA vaccine responses in ducks," Clin. Vaccine Immun. (2006) 13:958-965.
Gast, R.K. et al., "The relationship between the magnitude of the specific antibody response to experimental *Salmonella enteritidis* infection in laying hens and their production of contaminated eggs," Avian Diseases (2001) 45:425-431.
GenBank A0A086JZ08, "rhomboid protease 5" Oct. 2014.
GenBank AAT84606, "rhomboid protease 5 [Toxoplasma gondii]," May 8, 2014.
GenBank AF178849, "High mobility group protein HMG1 [Gallus gallus]," Sep. 27, 2000.
GenBank Q6GV23, "Rhomboid protease 5" May 2006.
GenBank Q7YZPO, "TRP250," Nov. 28, 2006.
Grangette, C. et al., Protection against tetanus toxin after intragastric administration of two recombinant lactic acid bacteria: Impact and strain viability and in vivo persistence, Vaccine (2002) 20:3304-3309.
Greenspan, N.S. et al., "Defining epitopes: It's not as easy as it seems," Nature Biotechnol. (1999) 17:936-937.
Grewal, I.S. et al., "CD40 and CD154 in cell-mediated immunity," Annu. Rev. Immunology. (1998) 16:111-35.
Harcourt, J.L. et al., "CD40 ligand (CD154) improves the durability of respiratory syncytial virus DNA vaccination in BALB/c mice," Vaccine (2003) 21(21-22):2964-2979.
Hargis, B, "Live Recombinant *Salmonella* Vaccination with Novel Universal Antigen Presentation and Immune Protection," USDA Grant Project Status, Jan. 14, 2012.
Harris, H.E. et al., "Mini-review: The nuclear protein HMGB1 as a proinflammatory mediator," European J. of Immunology (2004) 34:1503-1512.
Hayes, L.J. et al., "Chlamydia trachomatis major outer membrane protein epitopes expressed as fusions with LamB in an attenuated aro A strain of *Salmonella typhimurium*; their application as potential immunogens," Journal of General Microbiology (1991) 137:1557-1564.
Hoang, T.H. et al., "Recombinant Bacillus subtilis Expressing the Clostridium perfringens Alpha Toxoid Is a Candidate Orally Delivered Vaccine against Necrotic Enteritis," Infection and Immunity (2008) 76(11): 5257-5265.
Holmgren, J. et al., "Mucosal immunity: implications for vaccine development," Immunobiol. (1992) 184:157-179.
Husseiny, M.L. et al., "Rapid method for the construction of *Salmonella enterica* serovar *typhimurium* vaccine carrier strains," Infec. Immun. (2005) 73(3):1598-1605.
International Search Report and Written Opinion for Application No. PCT/US08/082254 dated Jun. 17, 2009 (12 pages).
International Search Report and Written Opinion for International Patent Application No. PCT/US2014/016359 dated May 23, 2014 (11 pages).
Saenz, R. et al., "HMGB1-derived peptide acts as adjuvant inducing immune responses to peptide and protein antigen," (2010) Vaccine 28(47):7556-7562.
Santos, J.M. & Soldati, D. Invasion factors are coupled to key signaling events leading to the establishment of infection in apicomplexan parasites. 2011 Cellular Microbiology:13(6), (787-96).
Shivaramaiah, S. et al., "Development and evaluation of an delta aroA I deltahtrA *Salmonella enteritidis* Vector Expressing *Eimeria maxima* TRAP Family Protein EmTFP250 with CD 154 (CD 40L) as Candidate Vaccines against Coccidiosis in Broilers," International Journal of Poultry Science (2010) 9(11): 1031-1037.
Smith, et al., ""Maternal transmission of immunity to *Eimeria maxima:* western blot analysis of protective antibodies induced by infection,"" Infect. Immun. (1994) 62:1348-1357.
Su, G.F. et al., "Construction of stable LamB-Shiga toxin B subunit hybrids: analysis of expression in *Salmonella typhimurium* aroA strains and stimulation of B subunit-specific mucosal and serum antibody responses," Infect Immun (1992) 60(8):3345-3359.
Swayne, D.E., "Vaccines for List A poultry diseases: emphasis on avian influenza," Dev. Biol. (2003) 114:201-212.
Tregaskes, C.A. et al., "Conservation of biological properties of the CD40 ligand, CD154 in a non-mammalian vertebrate," Dev. Comp. Immunol. (2005) 29:361-374.
Ulloa, L. et al., "High-mobility group box 1 (HMGB1) protein: friend and foe," Cytokine Growth Factor Rev. (2006) 17(3):189-201.
UniProt_G3LUI0_ROM4, Rhomboid-like protein, last modified Dec. 11, 2019.
UniProt_NCLIV_001580, Rhomboid-like protein, last modified Dec. 11, 2019.
Uyen, N.Q. et al., "Enhanced immunisation and expression strategies using bacterial spores as heat-stable vaccine delivery vehicles," Vaccine (2007) 25 356-365.
Vega, M.L. et al., "A *Salmonella typhi* OmpC fusion protein expressing the CD154 Trp140-Ser149 amino acid strand binds CD40 and activates a lymphoma B-cell line," Immunol. (2003) 110:206-216.
Verjans, G.M. et al., "Intracellular processing and presentation of T cell epitopes, expressed by recombinant *Escherichia coli* and *Salmonella typhimurium,* to human T cells," Eur J Immunol (1995) 25(2):405-410.
Vermeulen, A.N., "Progress in recombinant vaccine development against coccidiosis a review and prospects into the next millennium," International Journal of Parasitology (1998) 28:1121-1130.

(56) References Cited

OTHER PUBLICATIONS

Vierira-Pinto, M. et al . . . , "Occurrence of *Salmonella* in the ileum, ileocolic lymph nodes, tonsils, mandibular lymph nodes and carcasses of pigs slaughtered for consumption," J Vet Med B Infection Dis Vet Public Health (2005) 52 (10):476-81.

Wallach, M. et al., "Maternal immunization with gametocyte antigens as a means of providing protective immunity against *Emeria maxima* in chickens," Infection and Immunity, (1992) 60(5):2036-2039.

Wang, J et al., "Immunogenicity of viral B-cell epitopes inserted into two surface loops of the *Escherichia coli* K12 LamB protein and expressed in an attenuated aroA strain of *Salmonella typhimurium,*" Vaccine (1999) 17(1):1-12.

Wang, Q. et al., Protective immunity of recombinant *Mycobacterium bovis* BCG expressing rhomboid gene against *Eimeria tenella* challenge. Vet Parasitol, Nov. 13, 2008, vol. 160, No. 3-4, pp. 198-203.

Webster et al., "Safety of recombinant fowlpox strain FP9 and modified vacciniavirus Ankara vaccines against liver-stage *P. falciparum* malaria in non-immune volunteers," Vaccine (2006) 24:3026-3034.

Witcombe, D.M. et al., "*Eimeria maxima* TRAP family protein EmTFP250: subcellular localisation and induction of immune responses by immunization with a recombinant C-terminal derivative," Int. Jour. Parisitology (2004) 34(7):861-872; abstract, p. 862 fig 1.

Witcombe, D.M. et al., "Molecular characterisation of EmTFP250: A novel member of the TRAP protein family in *Eimeria maxima,*" International Journal of Parasitology (2003) 33(7):691-702.

Wolfenden et al., "Development and evaluation of candidate recombinant *Salmonella*-vectored *Salmonella* vaccines," Poult Sci (2010) 89(11):2370-9.

Xu, Y. et al., "The role of CD40-CD154 interaction in cell immunoregulation," J. Biomed. Sci. (2004) 11:426-438.

Yang, G. et al., *Eimeria tenella:* Construction of a recombinant fowlpox virus expressing rhomboid gene and its protective efficacy against homologous infection. 2007 Exp Parasitol 119(1):30-36.

Zhou, XW, et.al., (2004). Proteomic analysis of cleavage events revels a dynamic two-step mechanism for proteolysis of a key parasite adhesive complex. Molecular and Cellular Proteomics:3. 6(565-76).

Caoili, S.E.C., "Benchmarking B-Cell Epitope Prediction for the Design of Peptide-Based Vaccines: Problems and Prospects," Journal of Biomedicine and Biotechnology (2010) 2010:1-14.

Veronese, F. et al., "Loss of a Neutralizing Epitope by a Spontaneous Point Mutation in the V3 Loop of HIV-1 Isolated from an Infected Laboratory Worker*" Journal of Biological Chemistry (1993) 268(34):25894-25901.

Ossendorp, F. et al. "A single residue exchange within a viral CTL epitope alters proteasome-mediated degradation resulting in lack of antigen presentation" Immunity (1996) 5:115-124.

SEQUENCE LISTING

```
<160> NUMBER OF SEQ ID NOS: 40

<210> SEQ ID NO 1
<211> LENGTH: 16
<212> TYPE: PRT
<213> ORGANISM: Artificial sequence
<220> FEATURE:
<223> OTHER INFORMATION: Synthetic: composite minimal epitope
<220> FEATURE:
<221> NAME/KEY: misc_feature
```

<222> LOCATION: (2)..(2)
<223> OTHER INFORMATION: Xaa is Arg or Met
<220> FEATURE:
<221> NAME/KEY: misc_feature
<222> LOCATION: (3)..(4)
<223> OTHER INFORMATION: Xaa is Val or Ile
<220> FEATURE:
<221> NAME/KEY: misc_feature
<222> LOCATION: (5)..(5)
<223> OTHER INFORMATION: Xaa is Ser or Arg
<220> FEATURE:
<221> NAME/KEY: misc_feature
<222> LOCATION: (6)..(6)
<223> OTHER INFORMATION: Xaa is Phe or Tyr
<220> FEATURE:
<221> NAME/KEY: misc_feature
<222> LOCATION: (13)..(13)
<223> OTHER INFORMATION: Xaa is His or Tyr

<400> SEQUENCE: 1

```
Pro Xaa Xaa Xaa Xaa Xaa Gly Tyr Gly Ala Cys Glu Xaa Asn Leu Gly
1               5                   10                  15
```

<210> SEQ ID NO 2
<211> LENGTH: 43
<212> TYPE: PRT
<213> ORGANISM: Eimeria maxima
<220> FEATURE:
<221> NAME/KEY: misc_feature
<222> LOCATION: (1)..(43)
<223> OTHER INFORMATION: Eimeria maxima MPP

<400> SEQUENCE: 2

```
Pro Ser His Asp Ala Pro Glu Ser Glu Arg Thr Pro Arg Val Ile Ser
1               5                   10                  15

Phe Gly Tyr Gly Ala Cys Glu His Asn Leu Gly Val Ser Leu Phe Arg
            20                  25                  30

Arg Glu Glu Thr Lys Lys Asp Pro Arg Gly Arg
        35                  40
```

<210> SEQ ID NO 3
<211> LENGTH: 28
<212> TYPE: PRT
<213> ORGANISM: Neospora canium

<400> SEQUENCE: 3

```
Pro Arg Ile Val Ser Phe Gly Tyr Gly Ala Cys Glu His Asn Leu Gly
1               5                   10                  15

Met Ser Leu Tyr Asp Arg Gln Gly Leu Gln Arg Gln
            20                  25
```

<210> SEQ ID NO 4
<211> LENGTH: 21
<212> TYPE: PRT
<213> ORGANISM: Eimeria tenella

<400> SEQUENCE: 4

```
Glu Ser Gln Arg Ala Pro Met Val Ile Arg Tyr Gly Tyr Gly Ala Cys
1               5                   10                  15

Glu Tyr Asn Leu Gly
            20
```

<210> SEQ ID NO 5
<211> LENGTH: 10
<212> TYPE: PRT
<213> ORGANISM: Eimeria maxima
<220> FEATURE:

```
<221> NAME/KEY: misc_feature
<222> LOCATION: (1)..(10)
<223> OTHER INFORMATION: Eimeria maxima TRAP-1

<400> SEQUENCE: 5

Gly Gly Gly Phe Pro Thr Ala Ala Val Ala
1               5                   10


<210> SEQ ID NO 6
<211> LENGTH: 40
<212> TYPE: PRT
<213> ORGANISM: Eimeria maxima
<220> FEATURE:
<221> NAME/KEY: misc_feature
<222> LOCATION: (1)..(40)
<223> OTHER INFORMATION: Eimeria maxima TRAP-02

<400> SEQUENCE: 6

Ala Ala Pro Glu Thr Pro Ala Val Gln Pro Lys Pro Glu Glu Gly His
1               5                   10                  15

Glu Arg Pro Glu Pro Glu Glu Glu Glu Glu Lys Lys Glu Glu Gly Gly
            20                  25                  30

Gly Phe Pro Thr Ala Ala Val Ala
        35                  40


<210> SEQ ID NO 7
<211> LENGTH: 40
<212> TYPE: PRT
<213> ORGANISM: Eimeria maxima
<220> FEATURE:
<221> NAME/KEY: misc_feature
<222> LOCATION: (1)..(40)
<223> OTHER INFORMATION: Eimeria maxima TRAP-03

<400> SEQUENCE: 7

Gly Gly Gly Phe Pro Thr Ala Ala Val Ala Gly Gly Val Gly Gly Val
1               5                   10                  15

Leu Leu Ile Ala Ala Val Gly Gly Gly Val Ala Ala Phe Thr Ser Gly
            20                  25                  30

Gly Gly Gly Ala Gly Ala Gln Glu
        35                  40


<210> SEQ ID NO 8
<211> LENGTH: 70
<212> TYPE: PRT
<213> ORGANISM: Eimeria maxima
<220> FEATURE:
<221> NAME/KEY: misc_feature
<222> LOCATION: (1)..(70)
<223> OTHER INFORMATION: Eimeria maxima TRAP

<400> SEQUENCE: 8

Ala Ala Pro Glu Thr Pro Ala Val Gln Pro Lys Pro Glu Glu Gly His
1               5                   10                  15

Glu Arg Pro Glu Pro Glu Glu Glu Glu Glu Lys Lys Glu Glu Gly Gly
            20                  25                  30

Gly Phe Pro Thr Ala Ala Val Ala Gly Gly Val Gly Gly Val Leu Leu
        35                  40                  45

Ile Ala Ala Val Gly Gly Gly Val Ala Ala Phe Thr Ser Gly Gly Gly
    50                  55                  60

Gly Ala Gly Ala Gln Glu
65                  70
```

```
<210> SEQ ID NO 9
<211> LENGTH: 8
<212> TYPE: PRT
<213> ORGANISM: Avian Influenza
<220> FEATURE:
<221> NAME/KEY: misc_feature
<222> LOCATION: (1)..(8)
<223> OTHER INFORMATION: Avian Influenza virus m2e

<400> SEQUENCE: 9

Glu Val Glu Thr Pro Ile Arg Asn
1               5


<210> SEQ ID NO 10
<211> LENGTH: 8
<212> TYPE: PRT
<213> ORGANISM: Avian Influenza
<220> FEATURE:
<221> NAME/KEY: misc_feature
<222> LOCATION: (1)..(8)
<223> OTHER INFORMATION: Avian Influenza virus m2e

<400> SEQUENCE: 10

Glu Val Glu Thr Pro Thr Arg Asn
1               5


<210> SEQ ID NO 11
<211> LENGTH: 12
<212> TYPE: PRT
<213> ORGANISM: Avian Influenza
<220> FEATURE:
<221> NAME/KEY: misc_feature
<222> LOCATION: (1)..(12)
<223> OTHER INFORMATION: Avian Influenza virus HA5 UA

<400> SEQUENCE: 11

Leu Leu Ser Arg Ile Asn His Phe Glu Lys Ile Gln
1               5                   10


<210> SEQ ID NO 12
<211> LENGTH: 19
<212> TYPE: PRT
<213> ORGANISM: Avian Influenza
<220> FEATURE:
<221> NAME/KEY: misc_feature
<222> LOCATION: (1)..(19)
<223> OTHER INFORMATION: Avian Influenza virus HA5 LB

<400> SEQUENCE: 12

Ala Asn Pro Ala Asn Asp Leu Cys Tyr Pro Gly Asp Phe Asn Asp Tyr
1               5                   10                  15

Glu Glu Leu


<210> SEQ ID NO 13
<211> LENGTH: 16
<212> TYPE: PRT
<213> ORGANISM: Avian Influenza
<220> FEATURE:
<221> NAME/KEY: misc_feature
<222> LOCATION: (1)..(16)
<223> OTHER INFORMATION: Avian Influenza virus NP 54-69

<400> SEQUENCE: 13

Gly Arg Leu Ile Gln Asn Ser Ile Thr Ile Glu Arg Met Val Leu Ser
1               5                   10                  15


<210> SEQ ID NO 14
<211> LENGTH: 14
```

<212> TYPE: PRT
<213> ORGANISM: Avian Influenza
<220> FEATURE:
<221> NAME/KEY: misc_feature
<222> LOCATION: (1)..(14)
<223> OTHER INFORMATION: Avian Influenza virus NP 147-160

<400> SEQUENCE: 14

```
Thr Tyr Gln Arg Thr Arg Ala Leu Val Arg Thr Gly Met Asp
1               5                   10
```

<210> SEQ ID NO 15
<211> LENGTH: 190
<212> TYPE: PRT
<213> ORGANISM: Gallus gallus
<220> FEATURE:
<221> NAME/KEY: misc_feature
<222> LOCATION: (1)..(190)
<223> OTHER INFORMATION: Chicken HMGB1 amino acid

<400> SEQUENCE: 15

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Phe Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp Ala Gly Lys Lys Val Val Ala
                165                 170                 175

Lys Ala Glu Lys Ser Lys Lys Lys Lys Glu Glu Glu Glu Asp
            180                 185                 190
```

<210> SEQ ID NO 16
<211> LENGTH: 85
<212> TYPE: PRT
<213> ORGANISM: Artificial sequence
<220> FEATURE:
<223> OTHER INFORMATION: Synthetic: HMGB1 box a1

<400> SEQUENCE: 16

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45
```

-continued

```
Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr
                85


<210> SEQ ID NO 17
<211> LENGTH: 54
<212> TYPE: PRT
<213> ORGANISM: Artificial sequence
<220> FEATURE:
<223> OTHER INFORMATION: Synthetic: HMGB1 box a2

<400> SEQUENCE: 17

Pro Asp Ala Ser Val Asn Phe Ser Glu Phe Ser Lys Lys Cys Ser Glu
1               5                   10                  15

Arg Trp Lys Thr Met Ser Ser Lys Glu Lys Gly Lys Phe Glu Asp Met
            20                  25                  30

Ala Lys Ala Asp Lys Leu Arg Tyr Glu Lys Glu Met Lys Asn Tyr Val
        35                  40                  45

Pro Pro Lys Gly Glu Thr
    50


<210> SEQ ID NO 18
<211> LENGTH: 73
<212> TYPE: PRT
<213> ORGANISM: Artificial sequence
<220> FEATURE:
<223> OTHER INFORMATION: Synthetic: HMGB1 box b1

<400> SEQUENCE: 18

Lys Asp Pro Asn Ala Pro Lys Arg Pro Pro Ser Ala Phe Phe Leu Phe
1               5                   10                  15

Cys Ser Glu Phe Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
        35                  40                  45

Ala Asp Asp Lys Gln Pro Tyr Glu Lys Lys Ala Ala Lys Leu Lys Glu
    50                  55                  60

Lys Tyr Glu Lys Asp Ile Ala Ala Tyr
65                  70


<210> SEQ ID NO 19
<211> LENGTH: 69
<212> TYPE: PRT
<213> ORGANISM: Artificial sequence
<220> FEATURE:
<223> OTHER INFORMATION: Synthetic: HMGB1 box b2

<400> SEQUENCE: 19

Asn Ala Pro Lys Arg Pro Pro Ser Ala Phe Phe Leu Phe Cys Ser Glu
1               5                   10                  15

Phe Arg Pro Lys Ile Lys Gly Glu His Pro Gly Leu Ser Ile Gly Asp
            20                  25                  30

Val Ala Lys Lys Leu Gly Glu Met Trp Asn Asn Thr Ala Ala Asp Asp
        35                  40                  45

Lys Gln Pro Tyr Glu Lys Lys Ala Ala Lys Leu Lys Glu Lys Tyr Glu
    50                  55                  60

Lys Asp Ile Ala Ala
```

-continued

65

<210> SEQ ID NO 20
<211> LENGTH: 21
<212> TYPE: PRT
<213> ORGANISM: Artificial sequence
<220> FEATURE:
<223> OTHER INFORMATION: Synthetic: HMGB1 RAGE Binding domain

<400> SEQUENCE: 20

```
Lys Asp Pro Asn Ala Pro Lys Arg Pro Pro Ser Ala Phe Phe Leu Phe
1               5                   10                  15

Cys Ser Glu Phe Arg
            20
```

<210> SEQ ID NO 21
<211> LENGTH: 33
<212> TYPE: PRT
<213> ORGANISM: Artificial sequence
<220> FEATURE:
<223> OTHER INFORMATION: Synthetic: HMGB1 proinflammatory cytokine activity

<400> SEQUENCE: 21

```
Leu Lys Glu Lys Tyr Glu Lys Asp Ile Ala Ala Tyr Arg Ala Lys Gly
1               5                   10                  15

Lys Val Asp Ala Gly Lys Lys Val Val Ala Lys Ala Glu Lys Ser Lys
            20                  25                  30

Lys
```

<210> SEQ ID NO 22
<211> LENGTH: 215
<212> TYPE: PRT
<213> ORGANISM: Homo sapiens
<220> FEATURE:
<221> NAME/KEY: misc_feature
<222> LOCATION: (1)..(215)
<223> OTHER INFORMATION: HMGB1

<400> SEQUENCE: 22

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160
```

-continued

```
Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Asp Glu Glu
            180                 185                 190

Asp Glu Glu Asp Glu Glu Glu Glu Glu Asp Glu Glu Asp Glu Asp Glu
        195                 200                 205

Glu Glu Asp Asp Asp Asp Glu
    210                 215


<210> SEQ ID NO 23
<211> LENGTH: 205
<212> TYPE: PRT
<213> ORGANISM: Danio rerio
<220> FEATURE:
<221> NAME/KEY: misc_feature
<222> LOCATION: (1)..(205)
<223> OTHER INFORMATION: Zebra fish HMGB1

<400> SEQUENCE: 23

Met Gly Lys Asp Pro Thr Lys Pro Arg Gly Lys Met Ser Ser Tyr Ala
1               5                   10                  15

Tyr Phe Val Gln Thr Cys Arg Glu Glu His Lys Lys Lys His Pro Glu
            20                  25                  30

Ala Thr Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Leu Asp Lys Ala Arg Tyr Glu Arg Glu Met Lys Asn Tyr Ile Pro Pro
65                  70                  75                  80

Lys Gly Glu Lys Lys Lys Arg Phe Lys Asp Pro Asn Ala Pro Lys Arg
                85                  90                  95

Pro Pro Ser Ala Phe Phe Ile Phe Cys Ser Glu Phe Arg Pro Lys Val
            100                 105                 110

Lys Glu Glu Thr Pro Gly Leu Ser Ile Gly Asp Val Ala Lys Arg Leu
        115                 120                 125

Gly Glu Met Trp Asn Lys Ile Ser Ser Glu Glu Lys Gln Pro Tyr Glu
    130                 135                 140

Lys Lys Ala Ala Lys Leu Lys Glu Lys Tyr Glu Lys Asp Ile Ala Ala
145                 150                 155                 160

Tyr Arg Ser Lys Gly Lys Val Gly Gly Gly Ala Ala Lys Ala Pro Ser
                165                 170                 175

Lys Pro Asp Lys Ala Asn Asp Glu Asp Glu Asp Asp Asp Glu Glu Glu
            180                 185                 190

Asp Glu Asp Asp Asp Asp Glu Glu Glu Glu Asp Asp Glu
        195                 200                 205


<210> SEQ ID NO 24
<211> LENGTH: 272
<212> TYPE: PRT
<213> ORGANISM: Gallus gallus
<220> FEATURE:
<221> NAME/KEY: misc_feature
<222> LOCATION: (1)..(272)
<223> OTHER INFORMATION: CD154 chicken

<400> SEQUENCE: 24

Met Asn Glu Ala Tyr Ser Pro Ala Ala Pro Arg Pro Met Gly Ser Thr
1               5                   10                  15

Ser Pro Ser Thr Met Lys Met Phe Met Cys Phe Leu Ser Val Phe Met
```

```
            20                  25                  30

Val Val Gln Thr Ile Gly Thr Val Leu Phe Cys Leu Tyr Leu His Met
        35                  40                  45

Lys Met Asp Lys Met Glu Glu Val Leu Ser Leu Asn Glu Asp Tyr Ile
    50                  55                  60

Phe Leu Arg Lys Val Gln Lys Cys Gln Thr Gly Glu Asp Gln Lys Ser
65                  70                  75                  80

Thr Leu Leu Asp Cys Glu Lys Val Leu Lys Gly Phe Gln Asp Leu Gln
                85                  90                  95

Cys Lys Asp Arg Thr Ala Ser Glu Glu Leu Pro Lys Phe Glu Met His
            100                 105                 110

Arg Gly His Glu His Pro His Leu Lys Ser Arg Asn Glu Thr Ser Val
        115                 120                 125

Ala Glu Glu Lys Arg Gln Pro Ile Ala Thr His Leu Ala Gly Val Lys
    130                 135                 140

Ser Asn Thr Thr Val Arg Val Leu Lys Trp Met Thr Thr Ser Tyr Ala
145                 150                 155                 160

Pro Thr Ser Ser Leu Ile Ser Tyr His Glu Gly Lys Leu Lys Val Glu
                165                 170                 175

Lys Ala Gly Leu Tyr Tyr Ile Tyr Ser Gln Val Ser Phe Cys Thr Lys
            180                 185                 190

Ala Ala Ala Ser Ala Pro Phe Thr Leu Tyr Ile Tyr Leu Tyr Leu Pro
        195                 200                 205

Met Glu Glu Asp Arg Leu Leu Met Lys Gly Leu Asp Thr His Ser Thr
    210                 215                 220

Ser Thr Ala Leu Cys Glu Leu Gln Ser Ile Arg Glu Gly Gly Val Phe
225                 230                 235                 240

Glu Leu Arg Gln Gly Asp Met Val Phe Val Asn Val Thr Asp Ser Thr
                245                 250                 255

Ala Val Asn Val Asn Pro Gly Asn Thr Tyr Phe Gly Met Phe Lys Leu
            260                 265                 270


<210> SEQ ID NO 25
<211> LENGTH: 261
<212> TYPE: PRT
<213> ORGANISM: Homo sapiens
<220> FEATURE:
<221> NAME/KEY: misc_feature
<222> LOCATION: (1)..(261)
<223> OTHER INFORMATION: Human CD154

<400> SEQUENCE: 25

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110
```

```
Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260


<210> SEQ ID NO 26
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Human CD154 peptide

<400> SEQUENCE: 26

Trp Ala Glu Lys Gly Tyr Tyr Thr Met Ser Cys
1               5                   10


<210> SEQ ID NO 27
<211> LENGTH: 11
<212> TYPE: PRT
<213> ORGANISM: Gallus gallus
<220> FEATURE:
<221> NAME/KEY: misc_feature
<222> LOCATION: (1)..(11)
<223> OTHER INFORMATION: Chicken CD154 peptide

<400> SEQUENCE: 27

Trp Met Thr Thr Ser Tyr Ala Pro Thr Ser Ser
1               5                   10


<210> SEQ ID NO 28
<211> LENGTH: 10
<212> TYPE: PRT
<213> ORGANISM: Anas sp.
<220> FEATURE:
<221> NAME/KEY: misc_feature
<222> LOCATION: (1)..(10)
<223> OTHER INFORMATION: Duck CD154 peptide

<400> SEQUENCE: 28

Trp Asn Lys Thr Ser Tyr Ala Pro Met Asn
1               5                   10


<210> SEQ ID NO 29
<211> LENGTH: 10
```

<212> TYPE: PRT
<213> ORGANISM: Mus sp.
<220> FEATURE:
<221> NAME/KEY: misc_feature
<222> LOCATION: (1)..(10)
<223> OTHER INFORMATION: Mouse CD154 peptide

<400> SEQUENCE: 29

Trp Ala Lys Lys Gly Tyr Tyr Thr Met Lys
1               5                   10

<210> SEQ ID NO 30
<211> LENGTH: 10
<212> TYPE: PRT
<213> ORGANISM: Bos taurus
<220> FEATURE:
<221> NAME/KEY: misc_feature
<222> LOCATION: (1)..(10)
<223> OTHER INFORMATION: Cow CD154 peptide

<400> SEQUENCE: 30

Trp Ala Pro Lys Gly Tyr Tyr Thr Leu Ser
1               5                   10

<210> SEQ ID NO 31
<211> LENGTH: 918
<212> TYPE: DNA
<213> ORGANISM: Artificial sequence
<220> FEATURE:
<223> OTHER INFORMATION: Synthetic: TRAP MPP HMGB1 nucleotide sequence

<400> SEQUENCE: 31
ggatccatgg gcggtagcag cagaagcagc gcagcacctg aaacgagagc agtccagccg 60
aaacctgaag aaggccatga aagacctgaa cctgaagaag aagaagagaa aaaagaagaa 120
ggcggcggct ttcctacagc agcagtcgcg ggcggatcaa gcagatcttc cccttctcat 180
gatgcgcctg aaagcgaacg gacgcctcgg gttatctcct ttggttacgg tgcgtgcgaa 240
cataatctgg gcgtctctct ttttagacgc gaagaaacga aaaaagatcc gcgtggacgg 300
ggcggatcaa gcagatcttc catgggtaaa ggcgacccga aaaaacctcg gggcaaaatg 360
tcaagctacg catttttcgt ccaaacatgc agagaagaac ataagaaaaa acatcctgat 420
gctagcgtaa actttttcaga atttagcaaa aaatgttctg aacgttggaa aacgatgtct 480
tccaaagaaa agggtaaatt tgaagatatg gctaaagccg acaaattgcg gtacgaaaaa 540
gaaatgaaaa actacgtacc gcctaaagga gaaacaaaga aaaaatttaa agatccgaac 600
gcccctaaaa gaccgccttc tgcatttttc ctgttttgct ccgaatttcg cccgaaaatt 660
aaaggagaac atcctggtct gagcatcggc gacgttgcga aaaaacttgg agaaatgtgg 720
aataacacgg cagcggatga caaacagccg tatgagaaaa aagctgccaa attgaaagaa 780
aaatacgaaa aagatatcgc agcgtaccgc gcaaaaggaa aagtggacgc gggtaaaaaa 840
gttgtggcta aagcggaaaa atcaaagaag aaaaaggaag aagaagaaga cggcggctca 900
tctcggtcct ccgacgtc 918

<210> SEQ ID NO 32
<211> LENGTH: 306
<212> TYPE: PRT
<213> ORGANISM: Artificial sequence
<220> FEATURE:
<223> OTHER INFORMATION: Synthetic: TRAP MPP HMGB1 peptide

<400> SEQUENCE: 32

```
Gly Ser Met Gly Gly Ser Ser Arg Ser Ser Ala Ala Pro Glu Thr Arg
1               5                   10                  15

Ala Val Gln Pro Lys Pro Glu Glu Gly His Glu Arg Pro Glu Pro Glu
            20                  25                  30

Glu Glu Glu Glu Lys Lys Glu Glu Gly Gly Gly Phe Pro Thr Ala Ala
        35                  40                  45

Val Ala Gly Gly Ser Ser Arg Ser Ser Pro Ser His Asp Ala Pro Glu
    50                  55                  60

Ser Glu Arg Thr Pro Arg Val Ile Ser Phe Gly Tyr Gly Ala Cys Glu
65                  70                  75                  80

His Asn Leu Gly Val Ser Leu Phe Arg Arg Glu Glu Thr Lys Lys Asp
                85                  90                  95

Pro Arg Gly Arg Gly Gly Ser Ser Arg Ser Ser Met Gly Lys Gly Asp
            100                 105                 110

Pro Lys Lys Pro Arg Gly Lys Met Ser Ser Tyr Ala Phe Phe Val Gln
        115                 120                 125

Thr Cys Arg Glu Glu His Lys Lys Lys His Pro Asp Ala Ser Val Asn
    130                 135                 140

Phe Ser Glu Phe Ser Lys Lys Cys Ser Glu Arg Trp Lys Thr Met Ser
145                 150                 155                 160

Ser Lys Glu Lys Gly Lys Phe Glu Asp Met Ala Lys Ala Asp Lys Leu
                165                 170                 175

Arg Tyr Glu Lys Glu Met Lys Asn Tyr Val Pro Pro Lys Gly Glu Thr
            180                 185                 190

Lys Lys Lys Phe Lys Asp Pro Asn Ala Pro Lys Arg Pro Pro Ser Ala
        195                 200                 205

Phe Phe Leu Phe Cys Ser Glu Phe Arg Pro Lys Ile Lys Gly Glu His
    210                 215                 220

Pro Gly Leu Ser Ile Gly Asp Val Ala Lys Lys Leu Gly Glu Met Trp
225                 230                 235                 240

Asn Asn Thr Ala Ala Asp Asp Lys Gln Pro Tyr Glu Lys Lys Ala Ala
                245                 250                 255

Lys Leu Lys Glu Lys Tyr Glu Lys Asp Ile Ala Ala Tyr Arg Ala Lys
            260                 265                 270

Gly Lys Val Asp Ala Gly Lys Lys Val Val Ala Lys Ala Glu Lys Ser
        275                 280                 285

Lys Lys Lys Lys Glu Glu Glu Glu Asp Gly Gly Ser Ser Arg Ser Ser
    290                 295                 300

Asp Val
305
```

<210> SEQ ID NO 33
<211> LENGTH: 777
<212> TYPE: DNA
<213> ORGANISM: Artificial sequence
<220> FEATURE:
<223> OTHER INFORMATION: Synthetic: MPP HMGB1 nucleotide

<400> SEQUENCE: 33

```
ggatccatgg gcggtagcag cagaagcagc ccttctcatg atgcgcctga aagcgaacgg      60

acgcctcggg ttatctcctt tggttacggt gcgtgcgaac ataatctggg cgtctctctt     120

tttagacgcg aagaaacgaa aaaagatccg cgtggacggg gcggatcaag cagatcttcc     180

atgggtaaag gcgacccgaa aaaacctcgg ggcaaaatgt caagctacgc atttttcgtc     240

caaacatgca gagaagaaca taagaaaaaa catcctgatg ctagcgtaaa cttttcagaa     300
```

```
tttagcaaaa aatgttctga acgttggaaa acgatgtctt ccaaagaaaa gggtaaattt    360

gaagatatgg ctaaagccga caaattgcgg tacgaaaaag aaatgaaaaa ctacgtaccg    420

cctaaaggag aaacaaagaa aaaatttaaa gatccgaacg cccctaaaag accgccttct    480

gcatttttcc tgttttgctc cgaatttcgc ccgaaaatta aaggagaaca tcctggtctg    540

agcatcggcg acgttgcgaa aaaacttgga gaaatgtgga ataacacggc agcggatgac    600

aaacagccgt atgagaaaaa agctgccaaa ttgaaagaaa aatacgaaaa agatatcgca    660

gcgtaccgcg caaaaggaaa agtggacgcg ggtaaaaaag ttgtggctaa agcggaaaaa    720

tcaaagaaga aaaaggaaga agaagaagac ggcggctcat ctcggtcctc cgacgtc       777
```

```
<210> SEQ ID NO 34
<211> LENGTH: 259
<212> TYPE: PRT
<213> ORGANISM: Artificial sequence
<220> FEATURE:
<223> OTHER INFORMATION: Synthetic: MPP HMGB1 peptide

<400> SEQUENCE: 34

Gly Ser Met Gly Gly Ser Ser Arg Ser Ser Pro Ser His Asp Ala Pro
1               5                   10                  15

Glu Ser Glu Arg Thr Pro Arg Val Ile Ser Phe Gly Tyr Gly Ala Cys
            20                  25                  30

Glu His Asn Leu Gly Val Ser Leu Phe Arg Arg Glu Glu Thr Lys Lys
        35                  40                  45

Asp Pro Arg Gly Arg Gly Gly Ser Ser Arg Ser Ser Met Gly Lys Gly
    50                  55                  60

Asp Pro Lys Lys Pro Arg Gly Lys Met Ser Ser Tyr Ala Phe Phe Val
65                  70                  75                  80

Gln Thr Cys Arg Glu Glu His Lys Lys Lys His Pro Asp Ala Ser Val
                85                  90                  95

Asn Phe Ser Glu Phe Ser Lys Lys Cys Ser Glu Arg Trp Lys Thr Met
            100                 105                 110

Ser Ser Lys Glu Lys Gly Lys Phe Glu Asp Met Ala Lys Ala Asp Lys
        115                 120                 125

Leu Arg Tyr Glu Lys Glu Met Lys Asn Tyr Val Pro Pro Lys Gly Glu
    130                 135                 140

Thr Lys Lys Lys Phe Lys Asp Pro Asn Ala Pro Lys Arg Pro Pro Ser
145                 150                 155                 160

Ala Phe Phe Leu Phe Cys Ser Glu Phe Arg Pro Lys Ile Lys Gly Glu
                165                 170                 175

His Pro Gly Leu Ser Ile Gly Asp Val Ala Lys Lys Leu Gly Glu Met
            180                 185                 190

Trp Asn Asn Thr Ala Ala Asp Asp Lys Gln Pro Tyr Glu Lys Lys Ala
        195                 200                 205

Ala Lys Leu Lys Glu Lys Tyr Glu Lys Asp Ile Ala Ala Tyr Arg Ala
    210                 215                 220

Lys Gly Lys Val Asp Ala Gly Lys Lys Val Val Ala Lys Ala Glu Lys
225                 230                 235                 240

Ser Lys Lys Lys Lys Glu Glu Glu Glu Asp Gly Gly Ser Ser Arg Ser
                245                 250                 255

Ser Asp Val


<210> SEQ ID NO 35
```

```
<211> LENGTH: 768
<212> TYPE: DNA
<213> ORGANISM: Artificial sequence
<220> FEATURE:
<223> OTHER INFORMATION: Synthetic: TRAP HMGB1 nucleotide sequence

<400> SEQUENCE: 35

ggatccatgg gcggtagcag cagaagcagc gcagcacctg aaacgagagc agtccagccg     60

aaacctgaag aaggccatga aagacctgaa cctgaagaag aagaagagaa aaaagaagaa    120

ggcggcggct ttcctacagc agcagtcgcg ggcggatcaa gcagatcttc catgggtaaa    180

ggcgacccga aaaaacctcg ggcaaaatg tcaagctacg catttttcgt ccaaacatgc     240

agagaagaac ataagaaaaa acatcctgat gctagcgtaa acttttcaga atttagcaaa    300

aaatgttctg aacgttggaa aacgatgtct tccaaagaaa agggtaaatt tgaagatatg    360

gctaaagccg acaaattgcg gtacgaaaaa gaaatgaaaa actacgtacc gcctaaagga    420

gaaacaaaga aaaaatttaa agatccgaac gcccctaaaa gaccgccttc tgcatttttc    480

ctgttttgct ccgaatttcg cccgaaaatt aaaggagaac atcctggtct gagcatcggc    540

gacgttgcga aaaaacttgg agaaatgtgg aataacacgg cagcggatga caaacagccg    600

tatgagaaaa aagctgccaa attgaaagaa aaatacgaaa aagatatcgc agcgtaccgc    660

gcaaaaggaa aagtggacgc gggtaaaaaa gttgtggcta aagcggaaaa atcaaagaag    720

aaaaaggaag aagaagaaga cggcggctca tctcggtcct ccgacgtc                 768


<210> SEQ ID NO 36
<211> LENGTH: 256
<212> TYPE: PRT
<213> ORGANISM: Artificial sequence
<220> FEATURE:
<223> OTHER INFORMATION: Synthetic: TRAP HMGB1 peptide

<400> SEQUENCE: 36

Gly Ser Met Gly Gly Ser Ser Arg Ser Ser Ala Ala Pro Glu Thr Arg
1               5                   10                  15

Ala Val Gln Pro Lys Pro Glu Glu Gly His Glu Arg Pro Glu Pro Glu
            20                  25                  30

Glu Glu Glu Glu Lys Lys Glu Glu Gly Gly Gly Phe Pro Thr Ala Ala
        35                  40                  45

Val Ala Gly Gly Ser Ser Arg Ser Ser Met Gly Lys Gly Asp Pro Lys
    50                  55                  60

Lys Pro Arg Gly Lys Met Ser Ser Tyr Ala Phe Phe Val Gln Thr Cys
65                  70                  75                  80

Arg Glu Glu His Lys Lys Lys His Pro Asp Ala Ser Val Asn Phe Ser
                85                  90                  95

Glu Phe Ser Lys Lys Cys Ser Glu Arg Trp Lys Thr Met Ser Ser Lys
            100                 105                 110

Glu Lys Gly Lys Phe Glu Asp Met Ala Lys Ala Asp Lys Leu Arg Tyr
        115                 120                 125

Glu Lys Glu Met Lys Asn Tyr Val Pro Pro Lys Gly Glu Thr Lys Lys
    130                 135                 140

Lys Phe Lys Asp Pro Asn Ala Pro Lys Arg Pro Pro Ser Ala Phe Phe
145                 150                 155                 160

Leu Phe Cys Ser Glu Phe Arg Pro Lys Ile Lys Gly Glu His Pro Gly
                165                 170                 175

Leu Ser Ile Gly Asp Val Ala Lys Lys Leu Gly Glu Met Trp Asn Asn
            180                 185                 190
```

Thr Ala Ala Asp Asp Lys Gln Pro Tyr Glu Lys Lys Ala Ala Lys Leu
195 200 205

Lys Glu Lys Tyr Glu Lys Asp Ile Ala Ala Tyr Arg Ala Lys Gly Lys
210 215 220

Val Asp Ala Gly Lys Lys Val Val Ala Lys Ala Glu Lys Ser Lys Lys
225 230 235 240

Lys Lys Glu Glu Glu Glu Asp Gly Gly Ser Ser Arg Ser Ser Asp Val
245 250 255

<210> SEQ ID NO 37
<211> LENGTH: 32
<212> TYPE: PRT
<213> ORGANISM: Toxoplasma gondii
<220> FEATURE:
<221> NAME/KEY: misc_feature
<222> LOCATION: (1)..(32)
<223> OTHER INFORMATION: Toxoplasma gondii RH

<400> SEQUENCE: 37

Pro Arg Val Ile Ser Phe Gly Tyr Gly Ala Cys Glu His Asn Leu Gly
1 5 10 15

Val Ser Leu Phe Arg Arg Glu Glu Thr Lys Lys Asp Pro Arg Gly Arg
20 25 30

<210> SEQ ID NO 38
<211> LENGTH: 43
<212> TYPE: PRT
<213> ORGANISM: Artificial sequence
<220> FEATURE:
<223> OTHER INFORMATION: Synthetic: Consensus sequence
<220> FEATURE:
<221> NAME/KEY: misc_feature
<222> LOCATION: (11)..(11)
<223> OTHER INFORMATION: Xaa can be any amino acid
<220> FEATURE:
<221> NAME/KEY: misc_feature
<222> LOCATION: (13)..(17)
<223> OTHER INFORMATION: Xaa can be any amino acid
<220> FEATURE:
<221> NAME/KEY: misc_feature
<222> LOCATION: (24)..(24)
<223> OTHER INFORMATION: Xaa can be any amino acid
<220> FEATURE:
<221> NAME/KEY: misc_feature
<222> LOCATION: (28)..(28)
<223> OTHER INFORMATION: Xaa can be any amino acid
<220> FEATURE:
<221> NAME/KEY: misc_feature
<222> LOCATION: (31)..(32)
<223> OTHER INFORMATION: Xaa can be any amino acid
<220> FEATURE:
<221> NAME/KEY: misc_feature
<222> LOCATION: (35)..(39)
<223> OTHER INFORMATION: Xaa can be any amino acid

<400> SEQUENCE: 38

Pro Ser His Asp Ala Pro Glu Ser Glx Arg Xaa Pro Xaa Xaa Xaa Xaa
1 5 10 15

Xaa Gly Tyr Gly Ala Cys Glu Xaa Asn Leu Gly Xaa Ser Leu Xaa Xaa
20 25 30

Arg Glx Xaa Xaa Xaa Xaa Xaa Pro Arg Gly Arg
35 40

<210> SEQ ID NO 39
<211> LENGTH: 841
<212> TYPE: PRT
<213> ORGANISM: Toxoplasma gondii
<220> FEATURE:
<221> NAME/KEY: misc_feature
<222> LOCATION: (1)..(841)
<223> OTHER INFORMATION: Toxoplasma gondii ROM5

<400> SEQUENCE: 39

```
Met Ser Ser Lys Gly Gly Ser Ser Arg Leu Gly Ser Lys Asp Leu Lys
1               5                   10                  15

Lys Met Thr Ser Arg Thr Glu Arg Glu Leu Arg Asp Ser Gly Arg Val
            20                  25                  30

Arg Gly Glu Val Glu Arg Val Glu Lys Arg Leu Arg Ala Thr Ala Lys
        35                  40                  45

Val Lys Glu Gln Pro Pro Thr Gly Asp Tyr Lys Arg Arg Ala Leu Ala
    50                  55                  60

Ser Pro Gly Glu Thr Ala Ala Pro Thr Phe Leu Val Asp Ser Arg Gly
65                  70                  75                  80

Ile Pro Arg Lys Thr Ser Ser Thr Ala Pro Arg Lys Ala Thr Leu Arg
                85                  90                  95

Pro Ala Ser Ser Ser Pro Arg Leu Ala Ser Ser Ser Arg Pro Thr Glu
            100                 105                 110

Ser Thr Leu Pro Ser Ser Ser Ser Arg Ala Leu Gln Gly Ala Ser Ser
        115                 120                 125

Ser Ser Ser Ser Arg Pro Arg Arg Leu His Glu Ser Ala Ser Gly Arg
    130                 135                 140

Gly Gly Ser Gly Gly Ser Ala Gly Glu Leu Arg Gln Glu Lys Lys Arg
145                 150                 155                 160

Leu Pro Glu Leu Glu Ala Ala Glu Ala Ala Pro Ala Ser Cys Val Val
                165                 170                 175

Glu Leu Arg Asp Val Thr Ala Arg Lys Gly Arg Thr Ser Pro Ala Thr
            180                 185                 190

Pro Pro Glu Thr Ala Gly Ser Ser Val Cys Gly Gln Gly Ser His Ala
        195                 200                 205

Arg Thr Ala Glu Lys Leu Glu Glu Gly Thr Ala Ser His Arg Asp Gly
    210                 215                 220

Ser Arg Arg Gly Ser Val Asp Ala Glu Thr Trp Ala Thr Pro Gly Asp
225                 230                 235                 240

Gly Ser Ser Ser His Glu Phe Glu Ser Ser Pro Gln Arg Glu Glu Arg
                245                 250                 255

Met Gln Pro Gln Glu Thr Gly Arg Arg Glu Leu Ser Ser Glu Pro Arg
            260                 265                 270

Ser Gly Asp Leu Thr Lys Asn Gly Gly Asp Gly Gly Pro Arg Arg His
        275                 280                 285

Ser Cys Ala Trp Arg Lys Trp Arg Glu His Met Ile Gln Ser Phe Asp
    290                 295                 300

Ile Thr Thr His Pro Phe Pro Pro Arg Gly Asp Gly Ser Pro Arg Arg
305                 310                 315                 320

Gly Lys Phe Leu Met Ile Phe Leu Thr Ser Ser Val Leu Phe Phe Val
                325                 330                 335

Phe Leu Gln Glu Leu Val Leu Asn Val Thr Thr Phe Asn Gly Arg Cys
            340                 345                 350

Met Ser Pro Val Leu Tyr Pro Ser His Asp Ala Pro Glu Ser Glu Arg
        355                 360                 365

Thr Pro Arg Val Ile Ser Phe Gly Tyr Gly Ala Cys Glu His Asn Leu
    370                 375                 380
```

-continued

```
Gly Val Ser Leu Phe Arg Arg Glu Glu Thr Lys Lys Asp Pro Arg Gly
385                 390                 395                 400

Arg Trp Thr Pro Gly Pro Leu Thr Glu Arg Cys Ala Ser Gly Arg Cys
                405                 410                 415

Ala Ser Asp Asp Gly Trp Pro Ser Asp Leu Val Gln Arg Gly Arg Ala
            420                 425                 430

Gln Arg Ser Pro Ala Ala Phe Asp Ser Pro Asn Pro Arg Val Phe Ser
        435                 440                 445

Ser Leu Gly Ala Leu Asp Thr Asn Lys Val Arg Asn Tyr Gly Glu Met
    450                 455                 460

Phe Arg Val Val Trp Gly Met Phe Leu His Gly Gly Trp Met His Leu
465                 470                 475                 480

Leu Leu Asn Val Ser Cys Gln Ala Gln Thr Leu Trp Ile Leu Glu Pro
                485                 490                 495

Ala Trp Gly Phe Leu Arg Thr Leu Ser Leu Trp Ile Val Gly Gly Val
            500                 505                 510

Ser Gly Ser Leu Leu Ser Ala Val Ala Asn Pro Cys Thr Val Thr Val
        515                 520                 525

Gly Ser Ser Gly Ala Phe Tyr Gly Leu Leu Gly Ala Leu Val Pro Phe
    530                 535                 540

Ser Ile Glu Tyr Trp Asp His Ile Ala Ser Pro Ala Trp Phe Leu Phe
545                 550                 555                 560

Cys Val Ser Val Leu Val Met Val Ala Gln Phe Gly Asn Met Val Gly
                565                 570                 575

Val Gln Gly Val Asp Asn Asn Ala His Leu Gly Gly Leu Ile Gly Gly
            580                 585                 590

Leu Leu Phe Gly Phe Ala Thr Ile Arg Ser Val His Ala Phe Arg Trp
        595                 600                 605

Gln Gly Val Ala Glu Arg Met Ala Ser Ser Thr Leu Phe Trp Trp Met
    610                 615                 620

Phe Pro Ala Glu Lys Arg Arg Ser Leu Arg Glu Asp Asn Leu Gln Arg
625                 630                 635                 640

Val Ala Arg Glu Arg Glu Glu Arg Ser Ser Gly Arg Ile Pro Pro Pro
                645                 650                 655

Lys Phe Val Trp Lys Phe Arg Gly His Glu Arg Glu Trp Cys Val Arg
            660                 665                 670

Phe Ala Ala Ala Val Gly Leu Val Thr Phe Trp Ser Val Leu Trp Leu
        675                 680                 685

Tyr Leu Leu Val Pro Ser Tyr Tyr Glu Ser Leu Ser Ser Pro Pro Gly
    690                 695                 700

Asn Phe Ser Phe Leu Gly Ser Thr Gly Cys His Cys Cys Arg Val Gln
705                 710                 715                 720

Pro Phe Pro Gly Glu Glu Asp Lys Leu Pro Ala Phe His Pro Val Arg
                725                 730                 735

Val Asn Arg Gly Leu Phe Trp Cys Phe Val Ser Glu Gly Val Ala Asn
            740                 745                 750

Leu Phe Cys Gly Arg Ser Ser Ala Leu Asn Arg Gly Ala Asp Val Tyr
        755                 760                 765

Gly Gln Thr Arg Gln Phe Glu Glu Ala Leu Gly Asp Leu Pro Ser Ala
    770                 775                 780

Arg Ala Gly Glu Ala Pro Leu Arg Ile Ala Lys Glu Glu Gly Glu Ser
785                 790                 795                 800

Ala Ser Val Trp Gln Arg Leu Val Lys Ser Ala Lys Lys Thr Tyr Asn
```

-continued

```
            805                 810                 815

Ala Val Leu Gly Asn Thr Thr Thr Pro Ala Ala Pro Ser Ala Ala Glu
            820                 825                 830

Leu Ala Gln Gln Thr Arg Ala Gly Gln
        835                 840


<210> SEQ ID NO 40
<211> LENGTH: 40
<212> TYPE: PRT
<213> ORGANISM: Eimeria maxima
<220> FEATURE:
<221> NAME/KEY: misc_feature
<222> LOCATION: (1)..(40)
<223> OTHER INFORMATION: Eimeria maxima TRAP-02A

<400> SEQUENCE: 40

Ala Ala Pro Glu Thr Arg Ala Val Gln Pro Lys Pro Glu Glu Gly His
1               5                   10                  15

Glu Arg Pro Glu Pro Glu Glu Glu Glu Glu Lys Lys Glu Glu Gly Gly
            20                  25                  30

Gly Phe Pro Thr Ala Ala Val Ala
        35                  40
```

COMPOSITIONS AND METHODS OF ENHANCING IMMUNE RESPONSES TO *EIMERIA* OR LIMITING *EIMERIA* INFECTION

CROSS-REFERENCE TO RELATED APPLICATIONS

This patent application is a Divisional Application of U.S. patent application Ser. No. 17/023,795, filed Sep. 17, 2020, which is a Divisional Application of U.S. patent application Ser. No. 16/439,511, filed Jun. 12, 2019, and issuing as U.S. Pat. No. 10,792,351 on Oct. 6, 2020, which is a Divisional Application of U.S. patent application Ser. No. 15/877,598, filed Jan. 23, 2018, and issuing as U.S. Pat. No. 10,328,137 on Jun. 25, 2019, which is a Divisional Application of U.S. patent application Ser. No. 15/450,138, filed Mar. 6, 2017, and issuing as U.S. Pat. No. 9,884,099 on Feb. 6, 2018, which is a Divisional Application of U.S. patent application Ser. No. 14/768,011, filed Aug. 14, 2015, and issued as U.S. Pat. No. 9,603,915 on Mar. 28, 2017 which is a national stage filing under 35 U.S.C. 371 of International Application No. PCT/US2014/016359, filed Feb. 14, 2014, which claims the benefit of priority of U.S. Provisional Patent Application No. 61/764,681, filed Feb. 14, 2013, all of which are incorporated herein by reference in their entirety.

SEQUENCE LISTING

This application is being filed electronically via EFS-Web and includes an electronically submitted Sequence Listing in .txt format. The .txt file contains a sequence listing entitled "2014-02-13 5658-00201_ST25.txt" created on Feb. 13, 2014 and is 40.3 kilobytes in size. The Sequence Listing contained in this .txt file is part of the specification and is hereby incorporated by reference herein in its entirety.

INTRODUCTION

Coccidiosis, an infectious disease of poultry, swine, and cattle caused by apicomplexan protozoan parasites (*Eimeria* spp. and related parasites) presents problems worldwide. Coccidiosis is among the top ten infectious diseases of poultry in terms of its economic impact on the poultry industry with production losses estimated to be up to $2 billion annually. Other apicomplexan parasites also cause disease, including *Plasmodium, Cryptosporidium* and *Toxoplasma*, which are the causative agents of malaria, cryptosporidiosis and toxoplasmosis, respectively.

Typical signs of coccidiosis include rapid loss of appetite, reduction in weight, diarrhea and acute mortality. Outbreaks in a flock occur upon exposure to high levels of pathogen and in most cases, coccidiosis predisposes birds to secondary bacterial infections. Traditional methods of disease control include the administration of antibiotics and chemotherapeutic agents. However, with continuous usage, this has led to resistance issues. Antibiotic use also decreases social acceptance of poultry meat. Vaccination is a rational approach because of its ability to confer long-term protection, typically for the entire lifespan of commercial chickens.

Most commercially available vaccines against *Eimeria* are based on controlled low dosage of essentially fully virulent but drug-sensitive *Eimeria* parasites. Vaccination with current *Eimeria*-based vaccines produces substantial vaccine-reaction morbidity and economic losses in vaccinated flocks. Thus an effective low-virulence vaccine against

*Eimeria* is needed. An effective vaccine for *Eimeria* based on conserved immunogenic targets may also prove useful as a vaccine against other apicomplexan parasites.

SUMMARY

A vaccine vector comprising a first polynucleotide sequence encoding an Apicomplexan Rhomboid polypeptide and methods of using the same are provided herein.

In one aspect, a vaccine vector comprising a first polynucleotide encoding an Apicomlexan Rhomboid polypeptide or an immunogenic fragment thereof and a second polypeptide sequence encoding an immunostimulatory polypeptide is disclosed. The Apicomplexan Rhomboid polypeptide and the immunostimulatory polypeptide are suitably expressed on the surface of the vaccine vector. The Apicomplexan Rhomboid polypeptide may comprise SEQ ID NO: 1, SEQ ID NO: 2, SEQ ID NO: 3, SEQ ID NO: 4, SEQ ID NO: 37, SEQ ID NO: 38, an immunogenic fragment of at least one of SEQ ID NO: 1-4, 37-38 or combinations of SEQ ID NO: 1-4 and 37-38. The immunostimulatory polypeptide may be a CD154 polypeptide capable of binding CD40 or an HMGB1 polypeptide. The CD154 polypeptides include fewer than 50 amino acids and comprise amino acids 140-149 of CD154 or a homolog thereof.

In another aspect, a vaccine vector comprising a first polynucleotide encoding an Apicomlexan Rhomboid polypeptide of SEQ ID NO: 1, SEQ ID NO: 2, SEQ ID NO: 3, SEQ ID NO: 4, SEQ ID NO: 37, SEQ ID NO: 38, an immunogenic fragment of at least one of SEQ ID NO: 1-4 or 37-38 or combinations of SEQ ID NO: 1-4 or 37-38. The Apicomplexan Rhomboid polypeptide may be expressed on the surface of the vaccine vector.

Vaccine vectors according to the present invention may be a virus, yeast, bacterium, or liposome vector. Pharmaceutical compositions may be comprised of the vaccine vectors described herein and a pharmaceutically acceptable carrier.

In still another aspect, methods of enhancing the immune response against an Apicomplexan parasite in a subject by administering a vaccine vector described herein to the subject are provided. The enhanced immune response may be an enhanced antibody response, an enhanced T cell response or a combination thereof.

In a still further aspect, methods of reducing morbidity and mortality associated with infection with an apicomplexan parasite in a subject by administering a vaccine vector as described herein to the subject are provided. The vaccine vector is capable of reducing the morbidity and mortality associated with subsequent infection with an apicomplexan parasite in subjects administered the vaccine vector as compared to controls.

DETAILED DESCRIPTION

Figure 1:
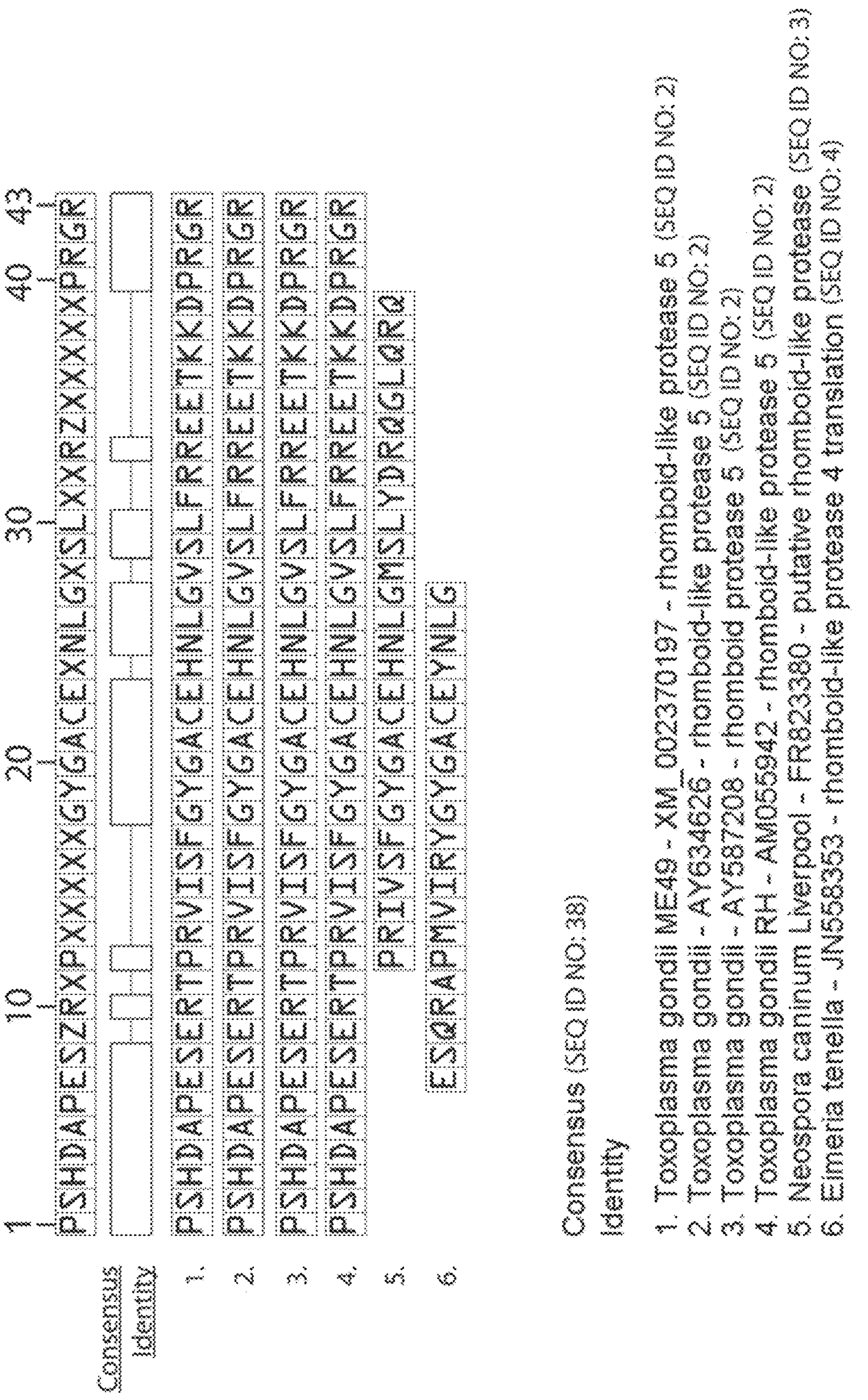
FIG. 1 is a schematic representation showing the homology of the MPP sequence among several Apicomplexan parasites. The consensus MPP sequence is highly similar in amino acid sequences in the Apicomplexans. Positions that are not identical are indicated with an X in the consensus sequence which is shown on the top line of the figure and is SEQ ID NO: 38. The *Toxoplasma gondii* sequences (the first four lines below the consensus) share 100% identity to the MPP sequence of SEQ ID NO: 2 from *Eimeria maxima*. The bottom two sequences are the homolog from *Neospora caninum* (SEQ ID NO: 3) and *Eimeria tenella* (SEQ ID NO: 4), respectively.

Conventional vaccines against coccidiosis are generally based on live/attenuated parasites that are delivered in controlled numbers. However, the risk of infection is not eliminated because the parasites are viable and capable of causing disease. Additionally, production costs for these types of vaccine are extremely high because it involves passing the parasites through live birds, collecting them at regular intervals and ensuring an uninterrupted cold transit chain from production to use at the hatchery or on the farm. With vaccination being a critical control method, the use of recombinant vaccines may improve the overall efficacy of coccidiosis-based vaccines while decreasing the production costs.

Species of *Eimeria* are highly immunogenic and are capable of stimulating robust host immune responses. The wide repertoire of antigens that are part of this eukaryote are highly specialized in function and are suitable targets for recombinant vaccine development. Sporozoites and merozoites are the most motile stages of the parasite and are responsible for initiating and sustaining an active infection. Invasion of these stages into intestinal epithelial cells is an essential process for the parasite to continue its life-cycle within host cells. A highly specialized set of organelles located at the anterior (apical) end of the parasite is involved in transporting the numerous proteins required for the translocation of these motile stages from the intestinal lumen into the epithelial layer. This apical complex consists of a variety of secretory organelles including a large number of micronemes that transport a milieu of proteins to the surface of motile apicomplexan zoites in support of the essential function of motility.

Among several well-described microneme-associated proteins, thrombospondin-related adhesive protein (TRAP) has been used as a successful recombinant antigen in *Salmonella* recombinant and *Bacillus*-vectored systems as a vaccine candidate. See U.S. Publication No. 2011/0111015, which is incorporated herein by reference in its entirety. Many microneme proteins have a similar mode of action in that they are released from the microneme complex at the anterior end of the sporozoite as they approach a host cell and act as a link between the parasite and whatever substrate they are upon. The microneme protein is then translocated across the surface of the parasite posteriorly, thereby moving the parasite closer to the host cell. This gliding form of motility is typical of all apicomplexan parasites. When the microneme protein has been translocated to the posterior end of the parasite, it needs to be cleaved and released from the surface of the parasite in order to successfully complete the invasion process. This function is performed by a family of proteases that are constitutively expressed within or on the parasite cell membrane. The cleavage process occurs intracellularly and is an absolute requirement for propagating the infection.

A novel approach to recombinant vaccine design involves targeting this protease and interfering with the cleavage/invasion process. The family of proteases that are involved in the cleavage process are called rhomboid proteases and are extremely well-described in *Toxoplasma* species with homologues in *Eimeria* and other Apicomplexa. Rhomboid proteases (ROM4 and ROM5, MPP) are centrally implicated in the cleavage of microneme proteins and share good homology among different apicomplexan parasites. Our hypothesis was based on the premise that if we are able to immunologically target the protease, antibody binding would interfere with the cleavage process and thereby impair sporozoite/merozoite mobility. For successful infection to occur, intracellular development of the parasite is essential and our approach may curtail cell invasion thus, interfering with establishment of the life-cycle. One advantage of targeting MPP is that the conserved nature of this protein across many apicomplexan species makes it a suitable target not only for *Eimeria*, but other Apicomplexa as well.

Predicted antigenic regions of MPP (ROM5) were aligned and checked for homology among six different Apicomplexa (FIG. 1). The seven sequences compared are as follows: *Eimeria tenella* ROM4 (JN558353). *Toxoplasma gondii* ME49 ROM5 (XP_002370238). *Toxoplasma gondii* ROM5 (AAT84606). *Toxoplasma gondii* ROM5 (AY587208). *Toxoplasma gondii* RH ROM5 (AM055942), *Toxoplasma gondii* (AY634626), and the MPP insert from *Eimeria maxima* of SEQ ID NO: 2. Suitable Apicomplexan parasites include, but are not limited to: *Eimeria* species, including but not limited to *Eimeria tenella, Eimeria maxima*, and *Eimeria brunetti; Toxoplasma gondii; Neospora caninum; Cryptosporidium* species; and *Plasmodium* species, including but not limited to *Plasmodium falciparum, Plasmodium malariae, Plasmodium knowlesi*, and *Plasmodium vivax.*

Recombinant DNA technologies enable relatively easy manipulation of many yeast, bacterial and viral species. Some microorganisms are mildly pathogenic or non-pathogenic, but are capable of generating a robust immune response. These microorganisms make attractive vaccine vectors for eliciting an immune response to antigens recombinantly expressed in the vector. Vaccines vectored by microorganisms may mimic a natural infection, help produce robust and long lasting mucosal immunity, and may be relatively inexpensive to produce and administer. In addition, such vectors can often carry more than one antigen and have potential to provide protection against multiple infectious agents.

In one aspect, a vaccine vector comprising a first polynucleotide sequence encoding an Apicomplexan Rhomboid polypeptide of SEQ ID NO: 1-4, 37-38, an immunogenic fragment thereof or combinations thereof is provided. In another embodiment, the vaccine vector may include a first polynucleotide encoding an Apicomplexan Rhomboid polypeptide and a second polynucleotide encoding an immunostimulatory polypeptide is provided. The Rhomboid polypeptide and the optional immunostimulatory polypeptide are expressed on the surface of the vaccine vector. The Rhomboid polypeptide may comprise the full-length protein (SEQ ID NO: 39) or an immunogenic fragment such as those provided in SEQ ID NO: 1-4 and 37-38. For example, the Rhomboid polypeptide may comprise, may consist essentially of or may consist of SEQ ID NO: 1, SEQ ID NO: 2. SEQ ID NO: 3, SEQ ID NO: 4, SEQ ID NO: 37, SEQ ID NO: 38 or an immunogenic fragment of any of these SEQ ID NOs. Combinations of these fragments may also be used in a vaccine vector. A vaccine vector may include SEQ ID NO: 1-4 or 37-38. A single vaccine vector may include multiple copies of a single fragment as well.

The immunogenic fragment of a Rhomboid polypeptide may be a sequence that is at least 5, 6, 7, 8, 10, 12, 14, 16, 18 or 20 amino acids long and has at least 85%, 90%, 92%, 94%, 95%, 96%, 97%, 98% or 99% percent identity to the fragments of SEQ ID NO: 1-4 or 37-38 provided herein. Without being limited by theory, the vaccine vectors provided herein are believed to be reducing morbidity and mortality associated with *Eimeria* infection by inducing an antibody response that is capable of blocking invasion of the parasites into cells. Those of skill in the art are aware that B cells epitopes are often hydrophilic in nature and this information can be used to generate immunogenic fragments to the polypeptides of SEQ ID NO: 1-4 and 37-38 provided herein. A hydrophilicity plot of SEQ ID NO: 2 reveals three hydrophilic areas of the peptide and three potential B cell epitopes including amino acids 1-11, 18-27 and 31-43 of SEQ ID NO: 2. These amino acid fragments correspond to amino acids 7-16 of SEQ ID NO: 3 and 37 and amino acids 12-21 of SEQ ID NO: 4. As shown by the two consensus sequences of SEQ ID NO: 1 and SEQ ID NO: 38, amino acids corresponding to 18-27 of SEQ ID NO: 2 am highly conserved across species and genera of Apicomplexan parasites. An immune response to such a highly conserved epitope may allow for cross species or even cross genera immunity from a single vaccine.

A vaccine includes any composition comprising a polynucleotide encoding an antigenic polypeptide that is capable of eliciting an immune response to the polypeptide. A vaccine vector is a composition that can be engineered to carry antigens or immunostimulatory polypeptides and may also comprise an adjuvant or be administered with an adjuvant to further increase the immune response to the parasite and provide better protection from morbidity and mortality associated with a subsequent infection. The use of vectors, such as bacterial vectors, for vaccination and generation of immune responses against *Eimeria* or other apicomplexan parasites such as *Plasmodium* (the causative agent of malaria), *Toxoplasma* and *Cryptosporidium* is disclosed. The immune responses after administration of the vaccine vector need not be fully protective, but may decrease the morbidity or percentage mortality (i.e. likelihood of mortality) associated with subsequent infection.

Polynucleotides encoding Rhomboid polypeptide antigens of SEQ ID NO: 1-4, 37-38 or fragments thereof and other antigens from any number of pathogenic organisms may be inserted into the vector and expressed in the vector. The expression of these polynucleotides by the vector will allow generation of antigenic polypeptides following immunization of the subject. The polynucleotides may be inserted into the chromosome of the vector or encoded on plasmids or other extrachromosomal DNA. Those of skill in the art will appreciate that numerous methodologies exist for obtaining expression of polynucleotides in vectors such as *Salmonella* or *Bacillus*. The polynucleotides may be operably connected to a promoter (e.g., a constitutive promoter, an inducible promoter, etc.) by methods known to those of skill in the art. Suitably, polynucleotides encoding the Rhomboid antigens are inserted into a vector, e.g., a bacterial vector, such that the polynucleotide is expressed.

The polynucleotides encoding the Rhomboid antigens may be inserted in frame in a polynucleotide encoding a transmembrane protein. The polynucleotide encoding the Rhomboid antigen is inserted into the vector polynucleotide sequence to allow expression of the Rhomboid antigen on the surface of the vector. For example, the polynucleotide encoding Rhomboid antigen may be inserted in frame into the vector polynucleotide in a region encoding an external loop region of a transmembrane protein such that the vector polynucleotide sequence remains in frame. In one embodiment, the first polynucleotide encoding the Rhomboid polypeptide may be inserted into loop 9 of the lamB gene of *Salmonella.*

In another embodiment, the first polynucleotide is inserted into or at a surface exposed end of a protein that is attached to the cell wall, but is not a transmembrane protein. The protein may be a secreted protein that is anchored or attached to the cell wall via a protein or lipid anchor. In the Examples, the MPP (SEQ ID NO: 2) polypeptide is inserted at the 3' end of the fibronectin binding protein (FbpB) of *Bacillus subtilis*. Alternatively, the first polynucleotide encoding the Rhomboid antigen may be inserted into a polynucleotide encoding a secreted polypeptide.

Those of skill in the art will appreciate that the polynucleotide encoding the Rhomboid antigen could be inserted in a wide variety of vector polynucleotides to provide expression and presentation of the Rhomboid antigen to the immune cells of a subject treated with the vaccine. The polynucleotide encoding the Rhomboid antigen may be included in a single copy or more than one copy. The multiple copies may be inserted in a single location or more than one location. Alternatively, multiple epitopes such as combinations of the Rhomboid antigens provided herein as SEQ ID NO: 1-4 and 37-38 or combinations of this epitope with other apicomplexan epitopes such as TRAP or epitopes from other pathogens may be inserted into the vector at the same or more than one location.

Suitably the first polynucleotide encodes a portion of the Rhomboid polypeptide, the entire Rhomboid polypeptide or more than one epitope from the Rhomboid polypeptide. The combination of epitopes from more than one polypeptide from a single parasite or pathogen or the combination of epitopes from related pathogens is specifically contemplated. The polynucleotide may be inserted into the vector and may be inserted as a fusion protein containing more than a single epitope. In the Examples, SEQ ID NOs: 2 and 15 (MPP-HMGB1) or SEQ ID NOs: 2, 40 and 15 (MPP-TRAP-HMGB1) were incorporated into a *Bacillus* vector. Suitably, the portion of the Rhomboid polypeptide inserted into the vector is an antigenic fragment. An antigenic fragment is a peptide or polypeptide capable of eliciting a cellular or humoral immune response or capable of reducing the morbidity or mortality associated with subsequent infection with the parasite.

An antigenic polypeptide or epitope includes any polypeptide that is immunogenic. The antigenic polypeptides include, but are not limited to, antigens that are pathogen-related, allergen-related, tumor-related or disease-related. Pathogens include viral, parasitic, fungal and bacterial pathogens as well as protein pathogens such as the prions. The antigenic polypeptides may be full-length proteins or portions thereof. It is well established that immune system recognition of many proteins is based on a relatively small number of amino acids, often referred to as the epitope. Epitopes may be only 4-8 amino acids long. Thus, the antigenic polypeptides described herein may be full-length proteins, four amino acid long epitopes or any portion between these extremes. In fact the antigenic polypeptide may include more than one epitope from a single pathogen or protein. The antigenic polypeptides may have at least 85%, 90%, 92%, 94%, 95%, 96%, 97%, 98% or 99% percent identity to the SEQ ID NOs provided herein. Suitably, an antigenic fragment of the Rhomboid antigen or polypeptide may be four, live, six, seven, eight, nine, 10 or more amino acids, 15 or more amino acids or 20 or more amino acids of the full-length protein sequence.

Multiple copies of the same epitope or multiple epitopes from the same or different proteins may be included in the vaccine vector. The epitopes in the vaccine vector may be related and homologous to allow targeting of multiple related pathogens with a single vaccine vector. It is envisioned that several epitopes or antigens from the same or different pathogens or diseases may be administered in combination in a single vaccine vector to generate an enhanced immune response against multiple antigens. Recombinant vaccine vectors may encode antigens from multiple pathogenic microorganisms, viruses or tumor associated antigens. Administration of vaccine vectors capable of expressing multiple antigens has the advantage of inducing immunity against two or more diseases at the same time, providing broader protection against multiple strains of a single pathogen or a more robust immune response against a single pathogen.

In the examples, the MPP antigen (SEQ ID NO: 2) was co-expressed in several of the vectors with a second antigenic polypeptide. A high molecular mass, asexual stage antigen from *Eimeria maxima* (EmTFP250) was demonstrated to be a target for maternal antibodies produced by breeding hens infected with this protozoan parasite. Analysis of the amino acid sequence of the antigen revealed a novel member of the TRAP (thrombospondin-related anonymous protein) family, containing 16 thrombospondin type-1 repeats and 31 epidermal growth factor-like calcium binding domains. See U.S. Patent Publication No. 2011/0111015. EnTFP250 or TRAP also contains two low complex, hydrophilic regions rich in glutamic acid and glycine residues, and a transmembrane domain/cytosolic tail associated with parasite gliding motility that is highly conserved within apicomplexan microneme proteins. Several potential epitopes were selected and am identified in SEQ ID NO: 1-3 and 11 of U.S. Patent Publication No. 2011/0111015 which are reproduced herein as SEQ ID NO: 5-8. SEQ ID NO: 40 was used in the Examples provided herein and is referred to as a TRAP antigen as well. SEQ ID NO: 40 and SEQ ID NO: 6 vary by a single amino acid. A proline at position 6 of SEQ ID NO: 6 is changed to an arginine at the same position 6 of SEQ ID NO: 40. This change was made to make the epitope more flexible and hydrophilic with the goal of making it a better antigen. Those of skill in the art may make other single amino acids changes to improve antigenicity within the scope of this invention. Due to the conserved nature of this antigen, expression of these epitopes by a vector may induce protective immunity against multiple apicomplexan parasites and administration of a vaccine vector comprising two distinct antigenic polypeptides may induce a more robust immune response.

Those of skill in the art will appreciate that the antigenic polypeptides from other pathogens may be used in the vaccine vectors to enhance the immune response against more than one pathogen by a single vaccine. It would be advantageous to administer a single vaccine directed against multiple pathogens. A vaccine capable of eliciting an immune response to an Apicomplexan parasite, such as *Eimeria*, in combination with Influenza. *Salmonella, Campylobacter* or other pathogens is envisioned.

For example, the second antigenic polypeptide may be an Influenza polypeptide, suitably it is an Influenza H5N1 polypeptide or a polypeptide associated with multiple strains of the Influenza virus such as a polypeptide of the Influenza M2 protein. The ectodomain of the Influenza A virus M2 protein, known as M2e, protrudes from the surface of the virus. The M2e portion of the M2 protein contains about 24 amino acids. The M2e polypeptide varies little from one isolate to the next within Influenza. In fact, only a few naturally occurring mutations in M2e have been isolated from infected humans since the 1918 flu epidemic. In addition, influenza viruses isolated from avian and swine hosts have different, yet still conserved, M2e sequences. For reviews of the M2e polypeptide sequences isolated from human, avian and swine hosts see Liu et al., Microbes and Infection 7:171-177 (2005) and Reid et al., J. Virol. 76:10717-10723 (2002) each of which are incorporated herein by reference in its entirety. Suitably the entire M2e polypeptide may be inserted into the vaccine vector or only a portion may be used. An eight amino acid polypeptide (LM2 having amino acid sequence: EVETPIRN, SEQ ID NO: 9 or its variant M2eA having amino acid sequence EVETPTRN, SEQ ID NO: 10) was incorporated into a vaccine vector and demonstrated to produce an antibody response after administration to chickens. See U.S. Publication No. 2011/0027309 which is incorporated herein by reference in its entirety.

Other suitable epitopes for inclusion in an Influenza A vaccine vector include, but are not limited to, polypeptides of the hemagglutinin (HA) or the nuclear protein (NP) of Influenza A. For example, the peptides of SEQ ID NO: 11. SEQ ID NO: 12. SEQ ID NO: 13 or SEQ ID NO: 14 may be included in a vaccine vector. One of skill in the art will appreciate that any of these sequences may be used in combination with any other epitope including epitopes derived from other pathogens or antigens.

Immunostimulatory molecules included as part of the vaccine vector could potentially activate parts of the immune system critical to long-lasting protection or provide an adjuvant effect. Immunostimulatory polypeptides may be polypeptides capable of stimulating a naïve or adaptive immune response. The immunostimulatory polypeptides are not natively associated with the vaccine vector and are polypeptides natively associated with a vertebrate immune system, such as that of the subject to which the vaccine will be administered. Two immunostimulatory polypeptides are described herein, namely CD154 and High Mobility Group Box 1 (HMGB1) polypeptides, but one of skill in the art will appreciate that other immunostimulatory polypeptides could be used or alternatively could be used in combination with those described herein.

Additional polynucleotides encoding polypeptides involved in triggering the immune system may also be included in a vaccine vector. The polynucleotides may encode immune system molecules known for their stimulatory effects, such as an interleukin, Tumor Necrosis Factor, interferon, complement, or another polynucleotide involved in immune-regulation. The vaccine may also include polynucleotides encoding peptides known to stimulate an immune response, such as the CD154 or HMGB1 polypeptides described herein.

HMGB1 is secreted by activated macrophages and damaged cells, and acts as a cytokine mediator of inflammation, affecting the innate immune response. Portions of the HMGB1 sequence have been included in the vaccine vectors described in the Examples. The HMGB1 (High Mobility Group Box-1) protein was first identified as a DNA-binding protein critical for DNA structure and stability. It is a ubiquitously expressed nuclear protein that binds DNA with no sequence specificity. The protein is highly conserved and found in plants to mammals. The zebrafish, chicken and human HMGB1 amino acid sequences are provided in SEQ ID NO: 23, SEQ ID NO: 15 and SEQ ID NO: 22, respectively. The sequence throughout mammals is highly conserved with 98% amino acid identity and the amino acid changes are conservative. Thus an HMGB1 protein from one species can likely substitute for that from another species functionally. The full-length HMGB1 protein or a portion thereof may be used as the HMGB1 polypeptide in the vaccine vectors described herein. HMGB1 has two DNA binding regions termed A box as shown in SEQ ID NO: 16 and 17 and B box as shown in SEQ ID NO: 18 and 19. See Andersson and Tracey. Annu. Rev. Immunol. 2011, 29:139-162, which is incorporated herein by reference in its entirety.

HMGB1 is a mediator of inflammation and serves as a signal of nuclear damage, such as from necrotic cells. HMGB1 can also be actively secreted by cells of the monocyte/macrophage lineage in a process requiring acetylation of the protein, translocation across the nucleus and secretion. Extracellular HMGB1 acts as a potent mediator of inflammation by signaling via the Receptor for Advanced Glycated End-products (RAGE) and via members of the Toll-like Receptor family (TLR), in particular TLR4. The RAGE binding activity has been identified and requires the polypeptide of SEQ ID NO: 20. TLR4 binding requires the cysteine at position 106 of SEQ ID NO: 15, which is found in the B box region of HMGB1.

The inflammatory activities of HMGB1 do not require the full-length protein and functional fragments have been identified. The B box has been shown to be sufficient to mediate the pro-inflammatory effects of HMGB1 and thus SEQ ID NO: 18 and 19 are HMGB1 polypeptides or functional fragments thereof within the context of the present invention. In addition, the RAGE binding site and the pro-inflammatory cytokine activity have been mapped to SEQ ID NO: 20 and SEQ ID NO: 21, respectively. Thus, these polypeptides are functional fragments of HMGB1 polypeptides in the context of the present invention.

Those of skill in the art are capable of identifying HMGB1 polypeptides and fragments thereof capable of stimulating pro-inflammatory cytokine activity, using methods such as those in International Publication No. WO02/092004, which is incorporated herein by reference in its entirety. Suitably, the HMGB1 polypeptide includes the RAGE binding domain at amino acids 150-183 of SEQ ID NO:15 (SEQ ID NO: 20 or a homolog thereof) and the pro-inflammatory cytokine activity domain between amino acids 89-109 of SEQ ID NO: 15 (SEQ ID NO: 21 or a homolog thereof). In particular, HMGB1 polypeptides and functional fragments or homologs thereof include polypeptides identical to, or at least 99% identical, at least 98% identical, at least 97% identical, at least 96% identical, at least 95% identical, at least 90% identical, at least 85% identical, or at least 80% identical to the HMGB1 polypeptides of SEQ ID NOs: 15 or 16-23.

As described in more detail below, a vaccine vector may include a CD154 polypeptide that is capable of binding CD40 in the subject and stimulating the subject to respond to the vector and its associated antigen. Involvement of dendritic cells (DCs) is essential for the initiation of a powerful immune response as they possess the unique ability to activate naïve T cells, causing T cell expansion and differentiation into effector cells. It is the role of the DC, which is an antigen presenting cell (APC) found in virtually all tissues of the body, to capture antigens, transport them to associated lymphoid tissue, and then present them to naïve T cells. Upon activation by DCs, T cells expand, differentiate into effector cells, leave the secondary immune organs, and enter peripheral tissues. Activated cytotoxic T cells (CTLs) are able to destroy virus-infected cells, tumor cells or even APCs infected with intracellular parasites (e.g., *Salmonella*) and have been shown to be critical in the protection against viral infection. CD40 is a member of the TNF-receptor family of molecules and is expressed on a variety of cell types, including professional antigen-presenting cells (APCs), such as DCs and B cells. Interaction of CD40 with its ligand CD154 is extremely important and stimulatory for both humoral and cellular immunity. Stimulation of DCs via CD40, expressed on the surface of DCs, can be simulated by anti-CD40 antibodies. In the body, however, this occurs by interaction with the natural ligand for CD40 (i.e. CD154) expressed on the surface of activated T-cells. Interestingly, the CD40-binding regions of CD154 have been identified. The CD40-binding region of CD154 may be expressed on the surface of a vector, such as a *Salmonella* or *Bacillus* vector, and results in an enhanced immune response against a co-presented peptide sequence as shown in the Examples provided herein and in U.S. Patent Publication No. 2011/0027309, which is incorporated herein by reference in its entirety. A CD154 polypeptide may be a portion of CD154 full-length protein or the entire CD154 protein. Suitably, the CD154 polypeptide is capable of binding CD40.

As discussed above, a CD154 polynucleotide encoding a CD154 polypeptide that is capable of enhancing the immune response to the antigen may be included in the vaccine. Suitably, the CD154 polypeptide is fewer than 50 amino acids long, more suitably fewer than 40, fewer than 30 or fewer than 20 amino acids in length. The polypeptide may be between 10 and 15 amino acids, between 10 and 20 amino acids or between 10 and 25 amino acids in length. The CD154 sequence and CD40 binding region are not highly conserved among the various species. The CD154 sequences of chicken and human are provided in SEQ ID NO: 24 and SEQ ID NO: 25, respectively.

The CD40 binding regions of CD154 have been determined for a number of species, including human, chicken, duck, mouse and cattle and are shown in SEQ ID NO: 26, SEQ ID NO: 27, SEQ ID NO: 28, SEQ ID NO: 29, and SEQ ID NO: 30, respectively. Although there is variability in the sequences in the CD40 binding region between species, the human CD154 polypeptide was able to enhance the immune response in chickens. Therefore, one may practice the invention using species specific CD154 polypeptides or a heterologous CD154 polypeptide. Thus the CD154 polypeptides of SEQ ID NO: 24-30 may be included in a vaccine vector or a polypeptide at least 99, 98, 97, %, 95, 93, 90 or 85% identical to the sequences of SEQ ID NO: 24-30 may be included in a vaccine vector.

The polypeptide from CD154 stimulates an immune response at least in part by binding to its receptor, CD40. A polypeptide homologous to the CD154 polypeptide which is expressed on immune cells of the subject and which is capable of binding to the CD40 receptor on macrophages and other antigen presenting cells. Binding of this ligand-receptor complex stimulates macrophage (and macrophage lineage cells such as dendritic cells) to enhance phagocytosis and antigen presentation while increasing cytokine secretions known to activate other local immune cells (such as B-lymphocytes). As such, molecules associated with the CD154 peptide are preferentially targeted for immune response and expanded antibody production.

The antigenic polypeptides and the immunostimulatory polypeptides are delivered via a vaccine vector. The vaccine vectors may be bacterial, yeast, viral or liposome-based vectors. Potential vaccine vectors include, but are not limited to, *Bacillus* (*Bacillus subtilis*), *Salmonella* (*Salmonella enteritidis*), *Shigella, Escherichia* (*E, coli*), *Yersinia, Bordetella, Lactococcus, Lactobacillus, Streptococcus, Vibrio* (*Vibrio cholerae*), *Listeria*, yeast such as *Saccharomyces*, or *Pichia*, adenovirus, poxvirus, herpesvirus, alphavirus, and adeno-associated virus. Live bacterial, yeast or viral vaccine vectors may still pose risks to immunocompromised individuals and require additional regulatory scrutiny. Thus use of vectors that are killed or inactivated or qualify as Generally Recognized As Safe (GRAS) organisms by the Food and Drug Administration (FDA) is desirable. The problem is generating a robust immune response using such vectors. Methods of inactivating or killing bacterial, yeast or viral vaccine vectors are known to those of skill in the art and include, but are not limited to methods such as formalin inactivation, antibiotic-based inactivation, heat treatment and ethanol treatment. By including an immunostimulatory polypeptide such as HMGB1 (high mobility group box 1) polypeptide on the surface of the vaccine vector we can generate a robust immune response against an apicomplexan parasite using a *Bacillus* spp. vector. In fact, the Examples demonstrate that this vector can be inactivated such that it cannot replicate and still elicit a robust immune response after administration. The vaccine vectors may be wild-type bacteria, yeasts or viruses that are not pathogenic. Alternatively the vectors may be attenuated such that the vector has limited ability to replicate in the host or is not capable of growing without supplemented media for more than a few generations. Those of skill in the art will appreciate that there are a variety of ways to attenuate vectors and means of doing so.

At least a portion of the antigenic polypeptide and at least a portion of the immunostimulatory polypeptide are present or expressed on the surface of the vaccine vector. Present on the surface of the vaccine vector includes polypeptides that are comprised within an external loop of a transmembrane protein, interacting with, e.g., covalently or chemically cross-linked to, a transmembrane protein, a membrane lipid or membrane anchored carbohydrate or polypeptide. A polypeptide can be comprised within a transmembrane protein by having the amino acids comprising the polypeptide linked via a peptide bond to the N-terminus, C-terminus or anywhere within the transmembrane protein (i.e. inserted between two amino acids of the transmembrane protein or in place of one or more amino acids of the transmembrane protein (i.e. deletion-insertion)). Suitably, the polypeptides may be inserted into an external loop of a transmembrane protein. Suitable transmembrane proteins are srlA, cotB and lamB, but those of skill in the art will appreciate many suitable transmembrane proteins are available. Polypeptides may be linked to a membrane or cell wall anchored protein or lipid such that the antigenic polypeptide and the immunostimulatory polypeptide are expressed on the surface of the vaccine vector.

As described above, polynucleotides encoding the antigenic or immunostimulatory polypeptides may be inserted into the chromosome of the vector or maintained extrachromosomally (e.g., on a plasmid. BAC or YAC). Those of skill in the art will appreciate that these polynucleotides can be inserted in frame in a variety of polynucleotides and expressed in different parts of the vector or may be secreted. The polynucleotide encoding the immunostimulatory polypeptide capable of enhancing the immune response to the antigenic polypeptide may also encode the antigenic polypeptide. The polynucleotide encoding the antigenic polypeptide may be linked to the polynucleotide encoding the immunostimulatory polypeptide, such that in the vector, the two polypeptides are portions of the same polypeptide, such as in a fusion protein. In the Examples, a polynucleotide encoding the antigenic polypeptide also encodes the immunostimulatory polypeptide. In one embodiment, the two polynucleotides encoding the polypeptides are both inserted in frame in loop 9 of the lamB gene of *Salmonella enteritidis* or another vaccine vector. Those of skill in the art will appreciate that bacterial polynucleotides encoding other transmembrane proteins and other loops of the lamB gene may also be used.

Alternatively, the polynucleotide encoding the antigenic polypeptide and/or the immunostimulatory polypeptide may be inserted into a secreted polypeptide that is displayed or presented on the surface of the vaccine vector through association with a protein, lipid or carbohydrate on the surface of the vaccine vector. Those of skill in the art will appreciate that the polynucleotide encoding the antigenic polypeptide and/or the immunostimulatory polypeptide could be inserted in a wide variety of vaccine vector polynucleotides to provide expression and presentation of the antigenic polypeptide and/or the immunostimulatory polypeptide to the immune cells of a subject treated with the vaccine vector by expression on the surface of the vaccine vector. The coding region of the Apicomplexan Rhomboid polypeptide and the immunostimulatory polypeptide can be fused to the C-terminus of the *Staphylococcus aureus* fibronectin binding protein containing a sorting motif for sortase from *Listeria*. This allows the secreted proteins to be anchored on the cell wall of gram positive bacteria such as *Bacillus*. See Nguyen and Schumann, J Biotechnol (2006) 122: 473-482, which is incorporated herein by reference in its entirety. This system was used in the Examples to allow expression of the Rhomboid polypeptide linked to HMGB1 on the surface of *Bacillus*. Other similar methods may also be used.

Alternatively, the polypeptides may be covalently or chemically linked to proteins, lipids or carbohydrates in the membrane, cell wall, or capsid if a viral vector is being used through methods available to persons of skill in the art. For example, di-sulfide bonds or biotin—avidin cross-linking could be used to present the antigenic and immunostimulatory polypeptides on the surface of a vaccine vector. Suitably, the antigenic polypeptide and the immunostimulatory polypeptide are part of a fusion protein. The two polypeptides may be directly linked via a peptide bond or may be separated by a linker, spacer, or a section of a third protein into which they are inserted in frame. In the Examples, an amino acid spacer was used between the polypeptides. A spacer may be between 2 and 20 amino acids, suitably between 4 and 10 amino acids, suitably between 6 and 8 amino acids. Suitably the amino acids in the spacer have a small side chain and are not charged, such as glycine, alanine or serine. In the Examples, a spacer including two glycine residues, two serine residues and arginine and two more serine residues was used. Those of skill in the art will appreciate other spacers could be used.

In the Examples, the vaccine vectors have the antigenic polypeptides (MPP and/or TRAP polypeptides) and the immunostimulatory polypeptide (either CD154 or HMGB1 or both) encoded on the same polynucleotide and in frame with each other. In alternative embodiments, the immunostimulatory polypeptide and the antigenic polypeptide may be encoded by distinct polynucleotides. Those of skill in the art will appreciate that a variety of methods may be used to obtain expression of the antigenic polypeptide and the HMGB1 polypeptide on the surface of the vaccine vector. Such methods are known to those skilled in the art.

Compositions comprising the vaccine vector and a pharmaceutically acceptable carrier are also provided. A pharmaceutically acceptable carrier is any carrier suitable for in vivo administration. Suitably, the pharmaceutically acceptable carrier is acceptable for oral, nasal or mucosal delivery. The pharmaceutically acceptable carrier may include water, buffered solutions, glucose solutions or bacterial culture fluids. Additional components of the compositions may suitably include excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The vaccine vector in the compositions may not be capable of replication, suitably the vaccine vector is inactivated or killed prior to addition to the composition.

Methods of enhancing immune responses in a subject by administering a vaccine vector are also provided. The vaccine vector may contain a first polynucleotide encoding an Aplicomplexan Rhomboid polypeptide and a second polynucleotide encoding an immunostimulatory polypeptide. The immunostimulatory polypeptide is suitably a polypeptide natively associated with a vertebrate immune system and involved in stimulating an immune response. The immunostimulatory polypeptide may stimulate the native or adaptive immune response of the subject. Suitably a HMGB1 polypeptide or a CD154 polypeptide as described more fully above may be used as the immunostimulatory polypeptide. In the methods provided herein, the vaccine vector comprising an Apicomplexan Rhomboid polypeptide and an immunostimulatory polypeptide is administered to a subject in an amount effective to enhance or effect an immune response of the subject to the vaccine vector and in particular to the antigenic Rhomboid polypeptide and suitably to the apicomplexan parasite. The enhanced immune response may include the antibody or T cell response. Suitably the immune response is a protective immune response, but the immune response may not be fully protective, but may be capable of reducing the morbidity or mortality associated with infection. The immunostimulatory polypeptides may be used to enhance the immune response in the subject to any foreign antigen or antigenic polypeptide present in the vaccine vector in addition to the Rhomboid polypeptide. One of skill in the art will appreciate that the immunostimulatory polypeptide could be used to enhance the immune response to more than one antigenic polypeptide present in a vaccine vector. Enhancing an immune response includes, but is not limited to, inducing a therapeutic or prophylactic effect that is mediated by the immune system of the subject. Specifically, enhancing an immune response may include, but is not limited to, enhanced production of antibodies, enhanced class switching of antibody heavy chains, maturation of antigen presenting cells, stimulation of helper T cells, stimulation of cytolytic T cells or induction of T and B cell memory.

Suitably, the vaccine vector contains a polynucleotide encoding a polypeptide including amino acids 150-183 and 89-109 of the HMGB1 polypeptide (SEQ ID NO: 15) or a homolog thereof. In the Examples, a 190 amino acid polypeptide of HMGB1 was used. Suitably, the polynucleotide encodes a HMGB1 polypeptide from the same species as the subject. Heterologous combinations of HMGB1 polypeptides and subjects (e.g. a human HMGB1 polypeptide for use in a chicken vaccine) may be useful in the methods of the invention because HMGB1 is highly conserved through a wide number of species. The HMGB1 polypeptide may be used to enhance the immune response to more than one antigenic polypeptide present in a vaccine vector. The polypeptide from HMGB1 stimulates an immune response at least in part by activating dendritic cells and macrophages and thus stimulating production of cytokines such as IL-1, IL-6, IFN-$\gamma$ and TNF-$\alpha$. In the Examples, a polypeptide of HMGB1 was expressed on the surface of the vaccine vector.

The vaccine vector may suitably contain a CD154 polypeptide capable of binding to CD40 and activating CD40. The vaccine comprising the polynucleotide encoding a CD154 polypeptide capable of binding to CD40 is administered to a subject in an amount effective to enhance or affect the immune response of the subject to the vaccine. Suitably, the vaccine contains a polynucleotide encoding a polypeptide including amino acids 140-149 of the human CD154 polypeptide (SEQ ID NO: 25) or a homolog thereof. As noted above, a homologue of amino acid 140-149 derived from one species may be used to stimulate an immune response in a distinct species. Suitably, the polynucleotide encodes a CD154 polypeptide from the same species as the subject. Suitably, a polynucleotide encoding the polypeptide of SEQ ID NO: 26 is used in human subjects, a polynucleotide encoding the polypeptide of SEQ ID NO: 27 is used in chickens, a polynucleotide encoding the polypeptide of SEQ ID NO: 28 is used in ducks, a polynucleotide encoding the polypeptide of SEQ ID NO: 29 is used in mice, and a polynucleotide encoding the polypeptide of SEQ ID NO: 30 is used in cows. The human CD154 polypeptide (SEQ ID NO: 26) has been used in a chicken vaccine and was demonstrated to enhance the immune response to a foreign antigen. Thus other heterologous combinations of CD154 polypeptides and subjects may be useful in the methods of the invention.

In addition, methods of enhancing an immune response against an apicomplexan parasite and methods of reducing morbidity associated with subsequent infection with an apicomplexan parasite are disclosed. Briefly, the methods comprise administering to a subject an effective amount of a vaccine vector comprising a first polynucleotide sequence encoding an Apicomplexan Rhomboid polypeptide. The vaccine vector may also include a second polynucleotide encoding an immunostimulatory polypeptide in an effective amount. The Rhomboid polypeptides may include SEQ ID NO: 1-4, 37, 38 or combinations or fragments thereof. The insertion of the Rhomboid polypeptides into the vector may be accomplished in a variety of ways known to those of skill in the art, including but not limited to the scarless site-directed mutation system described in BMC Biotechnol. 2007 Sep. 17: 7(1): 59, Scarless and Site-directed Mutagenesis in *Salmonella Enteritidis* chromosome, which is incorporated herein by reference in its entirety and the method used herein as described in Nguyen and Schumann J Biotechnol 2006 122: 473-482, which is incorporated herein by reference in its entirety. The vector may also be engineered to express the Rhomboid polypeptides in conjunction with other antigenic polypeptides from apicomplexan parasites such as TRAP or from other pathogens including viruses such as Influenza M2e or bacteria such as *Salmonella* or *E. coli*. In particular, a polypeptide of CD154 capable of binding CD40 or HMGB1 may be expressed by the vector to enhance the immune response of the subject to the Rhomboid polypeptide.

The compositions containing antigenic polypeptides may also be used to decrease the morbidity associated with subsequent infection by an apicomplexan parasite. The compositions may prevent the parasite from causing disease or may limit or reduce any associated morbidity in a subject to which the compositions or vaccine vectors described herein were administered. The compositions and vaccine vectors described herein may reduce the severity of subsequent disease by decreasing the length of disease, weight loss, severity of symptoms of the disease, decreasing the morbidity or mortality associated with the disease or reducing the likelihood of contracting the disease. The compositions may also reduce the spread of the parasite by inhibiting transmission. The morbidity or mortality associated with the disease after administration of the vaccine vectors described herein may be reduced by 25%, 30%, 40%, 50%, 60%, 70%, 80%, 90% or even 100% as compared to similar subjects not provided the vaccine vector.

For administration to animals or humans, the compositions may be administered by a variety of means including, but not limited to, intranasally, mucosally, by spraying, intradermally, parenterally, subcutaneously, intraperitonelly, intravenously, intracranially, orally, by aerosol or intramuscularly. Eye-drop administration, oral gavage or addition to drinking water or food is additionally suitable. For poultry, the compositions may be administered in ovo).

Some embodiments of the invention provide methods of enhancing immune responses in a subject. Suitable subjects may include, but are not limited to, vertebrates, suitably mammals, suitably a human, and birds, suitably poultry such as chickens or turkeys. Other animals such as cows, cats, dogs or pigs may also be used. Suitably, the subject is non-human and may be an agricultural animal.

The useful dosage of the vaccine to be administered will vary depending on the age, weight and species of the subject, the mode and route of administration and the type of pathogen against which an immune response is sought. The composition may be administered in any dose sufficient to evoke an immune response. It is envisioned that doses ranging from $10^3$ to $10^{10}$ vector copies (i.e. colony forming units or plaque forming units), from $10^4$ to $10^9$ vector copies, or from $10^5$ to $10^7$ vector copies are suitable.

The composition may be administered only once or may be administered two or more times to increase the immune response. For example, the composition may be administered two or more times separated by one week, two weeks, three weeks, 1 month, 2 months, 3 months, 6 months, 1 year or more. The vaccine vector may comprise viable microorganisms prior to administration, but in some embodiments the vector may be killed prior to administration. In some embodiments, the vector may be able to replicate in the subject, while in other embodiments the vector may not be capable of replicating in the subject. Methods of inactivating microorganisms used as vectors are known to those of skill in the art. For example a bacterial vaccine vector may be inactivated using formalin, ethanol, heat exposure, or antibiotics. Those of skill in the art may use other methods as well.

It is envisioned that several epitopes or antigens from the same or different pathogens may be administered in combination in a single vaccine to generate an enhanced immune response against multiple antigens. Recombinant vaccines may encode antigens from multiple pathogenic microorganisms, viruses or tumor associated antigens. Administration of vaccine capable of expressing multiple antigens has the advantage of inducing immunity against two or more diseases at the same time. For example, live attenuated bacteria provide a suitable vector for eliciting an immune response against multiple antigens from a single pathogen, e.g., TRAP (SEQ ID NO: 6) and MPP from *Eimeria* (SEQ ID NO: 2); or against multiple antigens from different pathogens. e.g., *Eimeria* and influenza or *Salmonella*.

Vaccine vectors may be constructed using exogenous polynucleotides encoding antigens which may be inserted into the vaccine vector at any non-essential site or alternatively may be carried on a plasmid or other extra chromosomal vehicle (e.g. a BAC or YAC) using methods well known in the art. One suitable site for insertion of polynucleotides is within external portions of transmembrane proteins or coupled to sequences that target the exogenous polynucleotide for secretory pathways and/or allow attachment to the cell wall. One example of a suitable transmembrane protein for insertion of polynucleotides is the lamB gene. One suitable method of cell wall attachment is provided in the Examples Exogenous polynucleotides include, but are not limited to, polynucleotides encoding antigens selected from pathogenic microorganisms or viruses and include polynucleotides that are expressed in such a way that an effective immune response is generated. Such polynucleotides may be derived from pathogenic viruses such as influenza (e.g., M2e, hemagglutinin, or neuraminidase), herpesviruses (e.g., the genes encoding the structural proteins of herpesviruses), retroviruses (e.g., the gp160 envelope protein), adenoviruses, paramyxoviruses, coronaviruses and the like. Exogenous polynucleotides can also be obtained from pathogenic bacteria, e.g., genes encoding bacterial proteins such as toxins, outer membrane proteins or other highly conserved proteins. Further, exogenous polynucleotides from parasites, such as other Apicomplexan parasites are attractive candidates for use in a vector vaccine.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including" "comprising," or "having," and variations thereof, is meant to encompass the elements listed thereafter and equivalents thereof, as well as additional elements.

Embodiments recited as "including," "comprising." or "having" certain elements are also contemplated as "consisting essentially of" and "consisting or" those certain elements. The terms "a", "an" and "the" may mean one or more than one unless specifically delineated.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

The following examples are meant only to be illustrative and are not meant as limitations on the scope of the invention or of the appended claims. All references, included patents, patent publications and non-patent literature, cited herein are hereby incorporated by reference in their entirety. Any conflict between statements in references and those made herein should be resolved in favor of the statements contained herein.

EXAMPLES

Example 1. Construction of Vaccine Vectors

Figure 2:
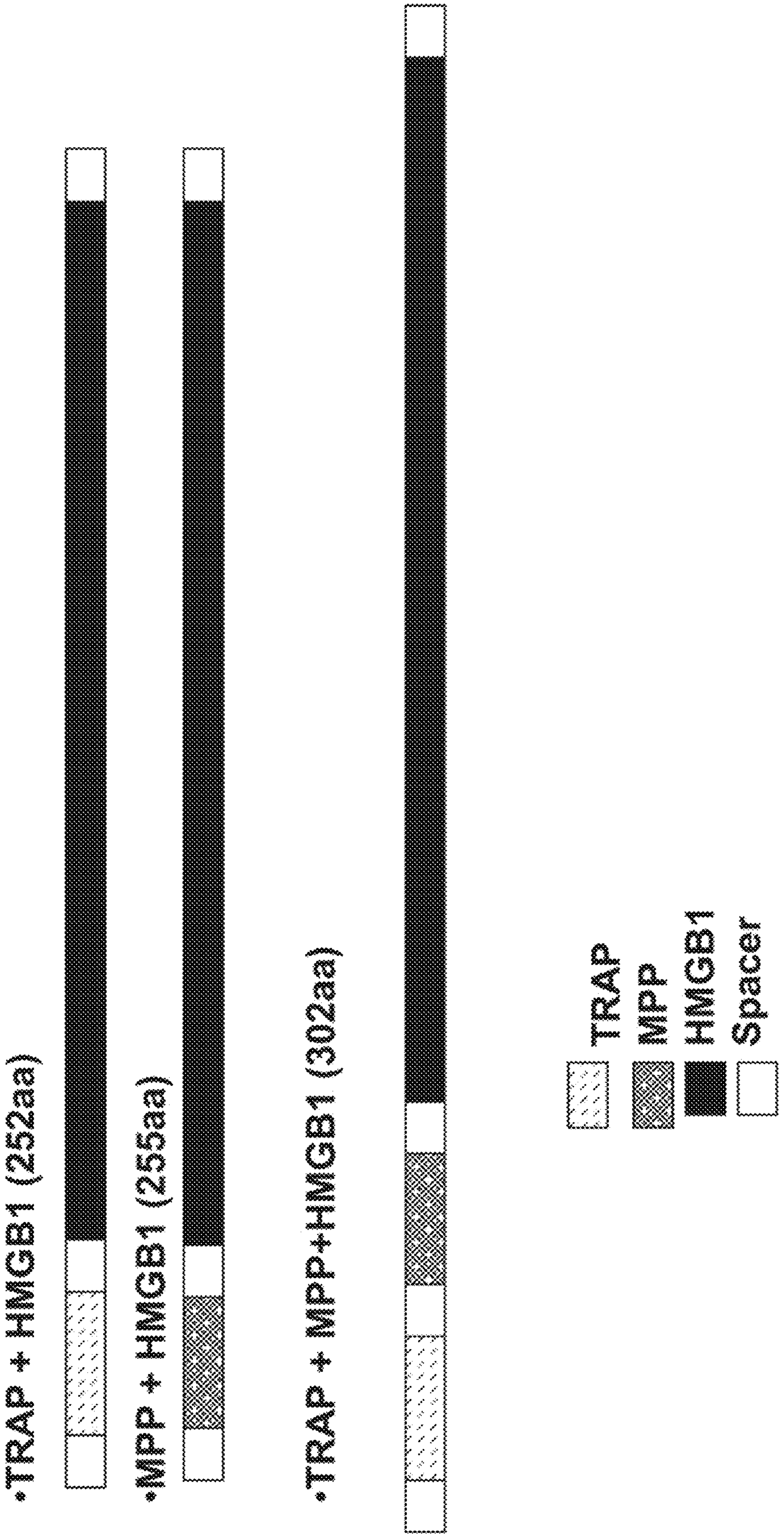
FIG. 2 is a schematic representation of the vaccine vector constructs described in the Examples.

Multiple combinations of vaccine were constructed for the purpose of testing efficacy and determining the influence of each on protection against *Eimeria maxima* challenge. A cartoon showing the constructs used in the examples is shown as FIG. 2. The TRAP MPP HMGB1, and MPP HMGB1 sequences were synthesized and inserted into pNDH10 plasmid for cell surface expression. Each sequence was synthesized with a BamH1 restriction site at the 5' end and an Aatl1 restriction site at the 3' end immediately adjacent to the fibronectin binding protein B (fbpB). Expression of the vaccine sequence and fbpB is regulated by a xyl operon previously inserted into pNDH10 plasmid [1]. The fbpB included a sorting motif that was recognized by sortase A that anchors the fbpB to the cell surface of a sortase A expressing bacterium [1]. Thus, the vaccine sequences are placed upstream and in frame with the fbpB sequence such that when the fbpB is anchored to sortase A on the cell wall the vaccine vector sequence will be expressed on the surface of the bacteria. Plasmid pNDH10 containing the vaccine sequence, fbpB, and xyl operon was transformed into *Bacillus subtilis* 1A857 expressing sortase A [2]. Each plasmid was transformed into 1A857 by adding 0.6 μg insert/plasmid into a competent 1A857 culture with 0.1 M ethylene glycol tetraacetic acid (EGTA). After transformation, 1A857 expressing pNDH10 were selected on LB agar containing 5 μg/mL chloramphenicol to select only cells that carried antibiotic resistance conferred by the plasmid via a cat sequence that encodes chloramphenicol acetyl transferase. *Bacillus subtilis* 1A857 transformed with MPP HMGB1 (SEQ ID NO: 33), or TRAP MPP HMGB1 (SEQ ID NO: 31) pNDH10 plasmids were confirmed by plasmid extraction followed by PCR. Each 1A857/pNDH10/insert construct was grown and induced in 0.6% xylose in LB broth +0.1% glucose with 5 μg/mL chloramphenicol for 9 h at 37° C. while shaking. MPP-HMGB1 (SEQ ID NO: 34) and TRAP-MPP-HMGB1 (SEQ ID NO: 32) protein expression were confirmed by Western blot and indirect fluorescence microscopy with rabbit anti-HMGB1 antibodies.

Figure 3:
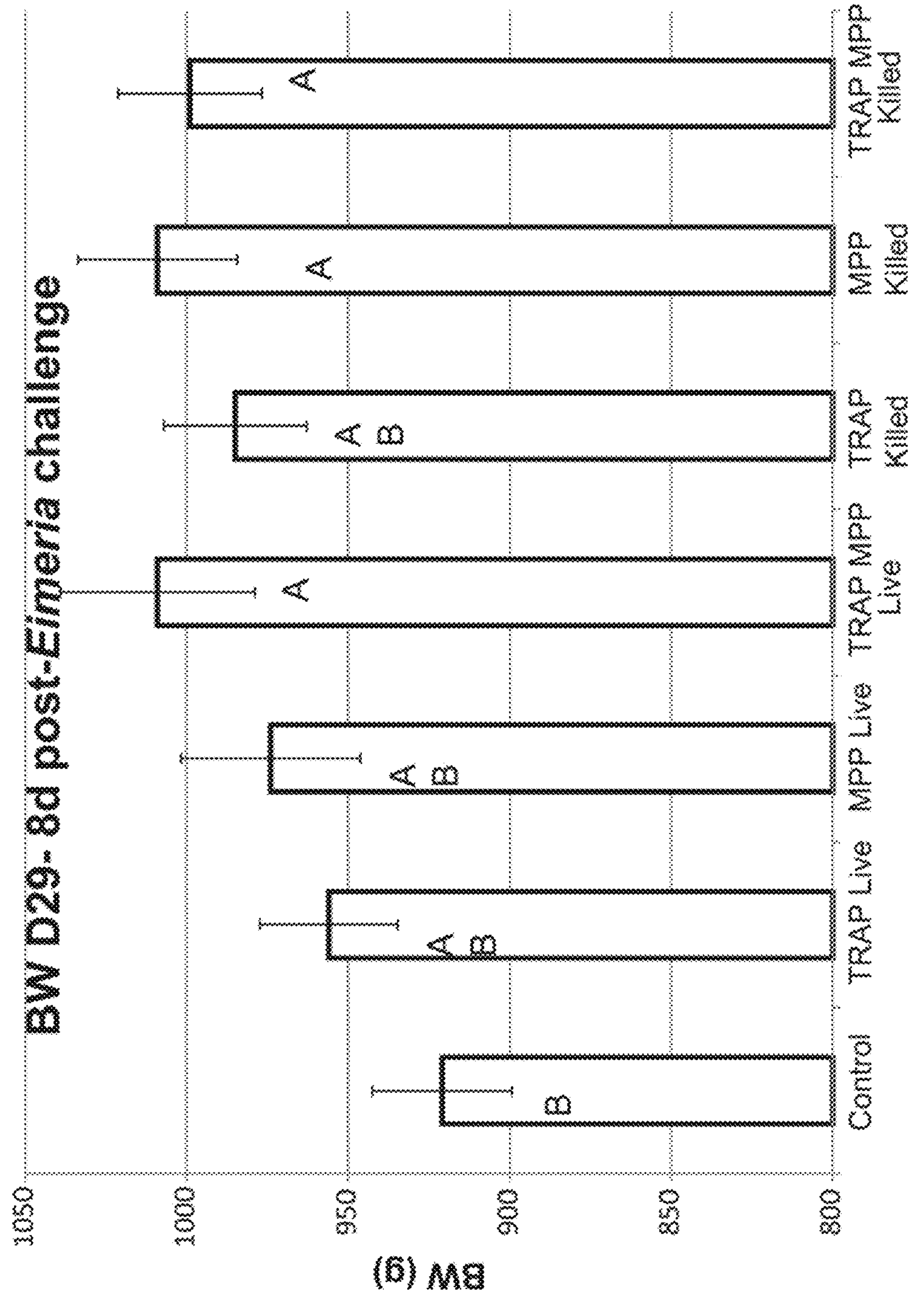
FIG. 3 is a bar graph showing the body weight (grams) of the chickens eight days post-infection with *Eimeria maxima* after inoculation with the indicated vaccine vector expressing the indicated sequences. Significant differences ($p<0.05$) between treatment groups are indicated by different letters.
Figure 4:
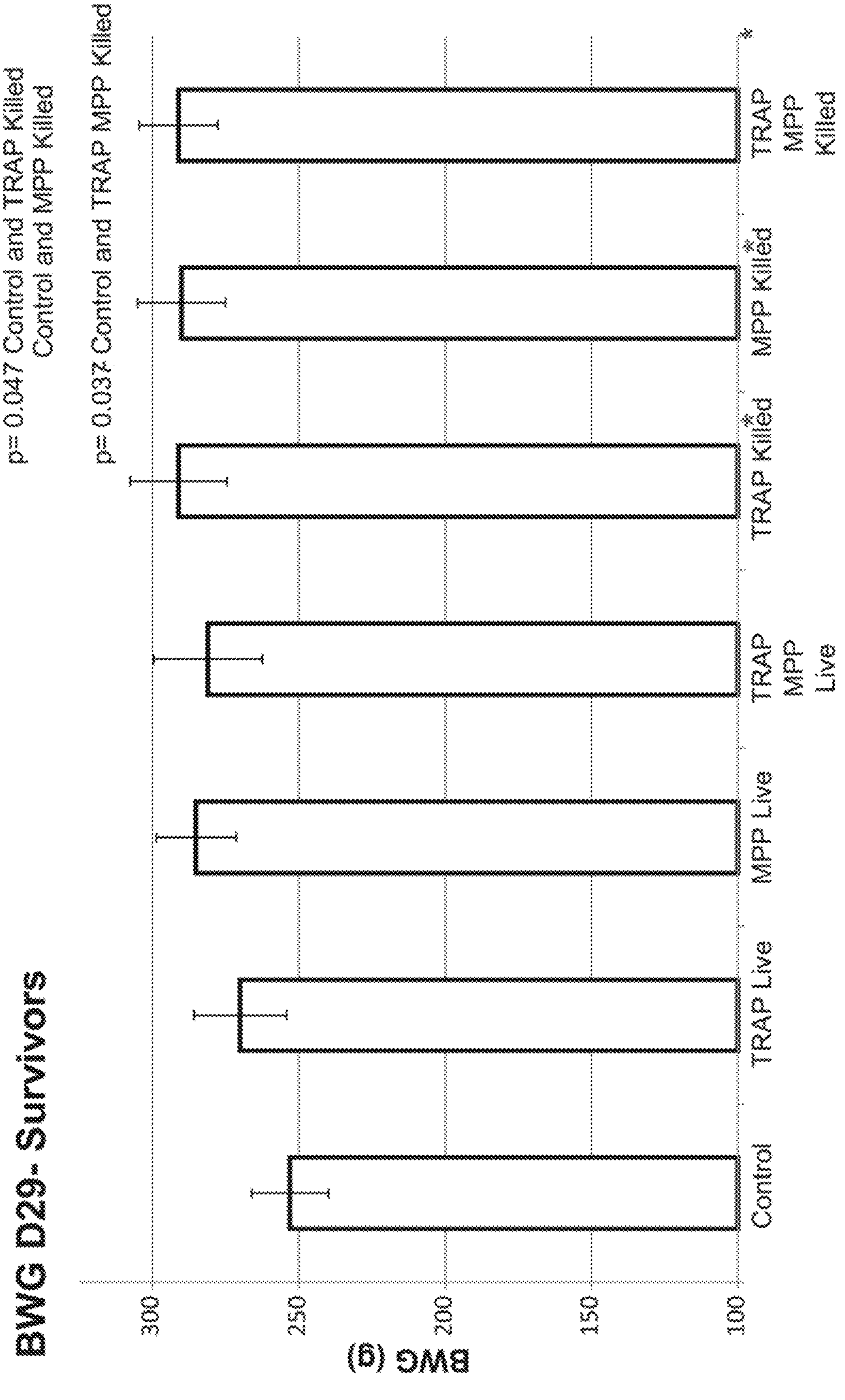
FIG. 4 is a bar graph showing the body weight (grams) of the surviving chickens 29 days post-challenge infection with *Eimeria maxima* after inoculation with the indicated vaccine vector expressing the indicated sequences. Significant differences ($p<0.05$) between treatment groups are indicated by actual p values and an asterisk (*).
Figure 5:
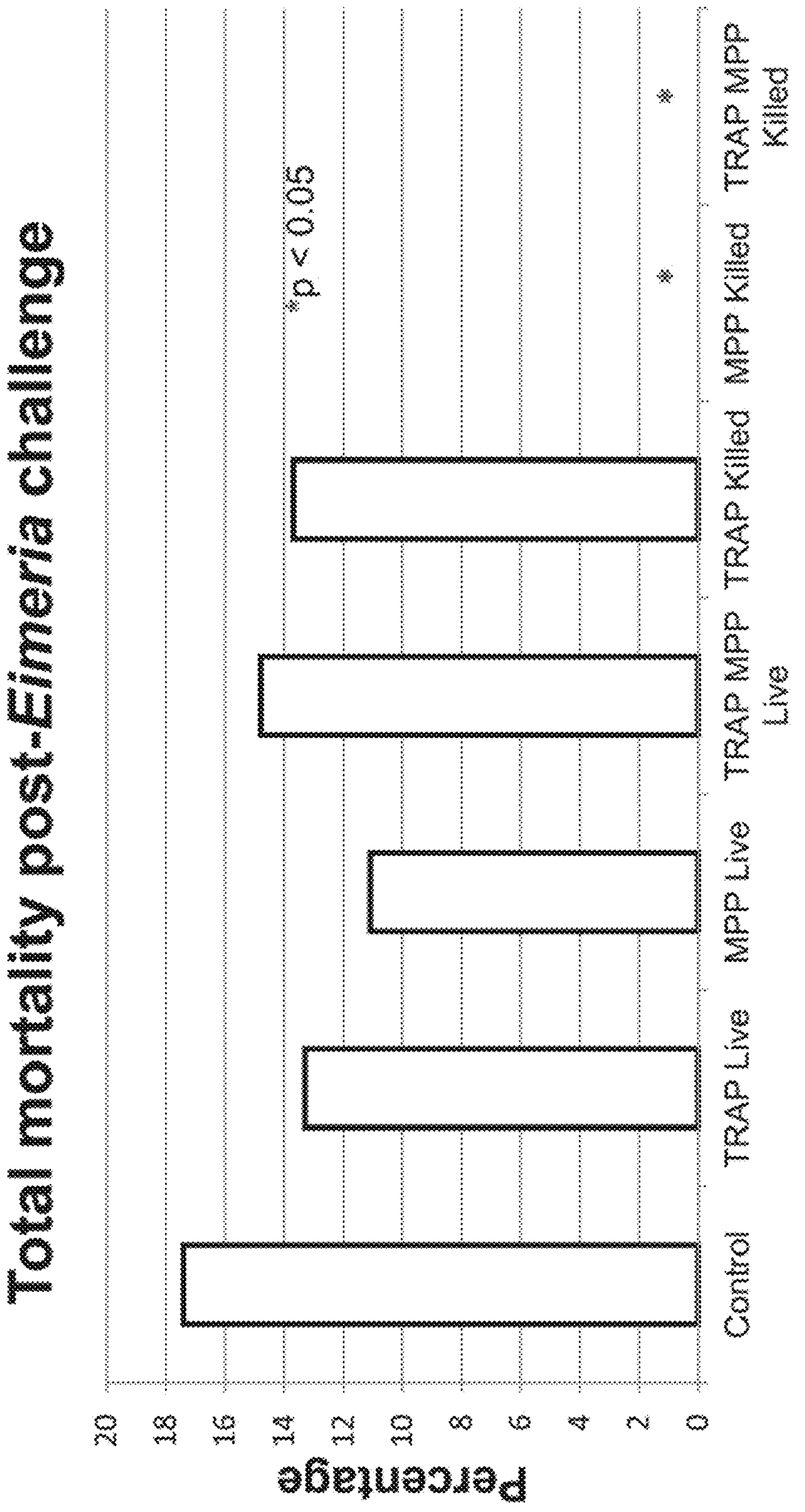
FIG. 5 is a bar graph showing the percent mortality in the face of a virulent challenge infection with *Eimeria* marina at eight days post-challenge infection with *Eimeria maxima* after inoculation with the indicated vaccine vector expressing the indicated sequences. Significant differences ($p<0.05$) are indicated with an asterisk (*).

Example 2. Reduced Morbidity and Mortality of Chicks after *Eimeria* Infection Vectored vaccines MPP HMGB1 and TRAP MPP HMGB1 were tested for ability to provide protection against an *Eimeria maxima* challenge when administered through the drinking water in conjunction with a modified chitosan adjuvant. Broiler chicks were vaccinated at 4 and 14 days of age with the respective vaccine in the drinking water at a dilution of 1:128 ($5\times10^5$ cfu/chick) for 24 h. At 21 d of age, all groups were weighed and challenged with $4\times10^4$ sporulated oocysts of *E. maxima* by oral gavage. At 28 d of age, body weight (BW) and body weight gain of survivors (BWG) were recorded during the challenge period. Additionally, mortality was documented to determine vaccine candidate efficacy. Eight days post-challenge BW was significantly higher in chicks vaccinated with TRAP-MPP-HMGB1 and MPP-HMGB1 when compared with non-vaccinated chicks (FIG. 3). BWG was significantly higher for all vaccinated groups 8d post-challenge when compared to controls (FIG. 4). Mortality was also significantly lower in the TRAP-MPP-HMGB1 and MPP-HMGB1 vaccinated groups with the unvaccinated group (FIG. 5).

[1] Kim L, Mogk A. Schumann W. A xylose-inducible *Bacillus subtilis* integration vector and its application. Gene 1996 Nov. 28; 181(1-2):71-6.

[2] Nguyen H D, Schumann W. Establishment of an experimental system allowing immobilization of proteins on the surface of *Bacillus subtilis* cells. Journal of biotechnology 2006 Apr. 20; 122(4):473-82.

We claim:

1. A vaccine vector comprising a first polynucleotide sequence encoding an apicomplexan rhomboid polypeptide expressed on the surface of the vaccine vector, wherein the Rhomboid polypeptide consists of a polypeptide having greater than 90% sequence identity to an amino acid sequence selected from the group consisting of SEQ ID NO: 37, an immunogenic fragment of SEQ ID NO: 37 comprising at least 14 amino acids of SEQ ID NO: 37, and an immunogenic fragment of SEQ ID NO: 37 comprising amino acids 7-16 or 20-32 of SEQ ID NO: 37.

2. The vaccine vector of claim 1 further comprising a second polynucleotide sequence encoding an immunostimulatory polypeptide, wherein the immunostimulatory polypeptide is expressed on the surface of the vaccine vector, and wherein an immunostimulatory polypeptide comprises a polypeptide capable of stimulating an immune response.

3. The vaccine vector of claim 2, wherein the immunostimulatory polypeptide comprises an HMGB1 polypeptide.

4. The vaccine vector of claim 3, wherein the HMGB1 polypeptide comprises a polypeptide selected from the group consisting of SEQ ID NOs: 15-23, a polypeptide having at least 95% sequence identity to SEQ ID NO: 15-23 and combinations thereof.

5. The vaccine vector of claim 2, wherein the immunostimulatory polypeptide comprises a CD154 polypeptide capable of binding CD40, the CD154 polypeptide having fewer than 50 amino acids and comprising amino acids 140-149 of a polypeptide selected from the group consisting of SEQ ID NO: 24, SEQ ID NO: 25, SEQ ID NO: 26, SEQ ID NO: 27, SEQ ID NO: 28, SEQ ID NO: 29, SEQ ID NO: 30, and polypeptides having at least 90% sequence identity to at least one of SEQ ID NOs: 24-30.

6. The vaccine vector of claim 2, wherein the vector comprises more than one copy of the first polynucleotide or more than one copy of the second polynucleotide sequence.

7. The vaccine vector of claim 2, wherein the first polynucleotide sequence is linked in the same reading frame to the second polynucleotide sequence.

8. The vaccine vector of claim 7, wherein the first polynucleotide and the second polynucleotide are linked via a spacer nucleotide sequence.

9. The vaccine vector of claim 1, wherein the vaccine vector is selected from the group consisting of a virus, a bacterium, a yeast, and a liposome.

10. The vaccine vector of claim 9, wherein the vaccine vector is a Bacillus spp.

11. The vaccine vector of claim 1, further comprising a third polynucleotide encoding a TRAP polypeptide selected from the group consisting of polypeptides having at least 95% sequence identity to SEQ ID NO: 5, SEQ ID NO: 6, SEQ ID NO: 7, and SEQ ID NO: 40.

12. A pharmaceutical composition comprising the vaccine vector of claim 1 and a pharmaceutically acceptable carrier.

13. A method of enhancing the immune response against an apicomplexan parasite in a subject comprising administering to the subject the vaccine vector of claim 1 in an amount effective to enhance the immune response of the subject to the apicomplexan parasite.

14. The method of claim 13, wherein the enhanced immune response comprises an enhanced antibody response, an enhanced T cell response or both.

15. A method of reducing morbidity associated with infection with an apicomplexan parasite in a subject comprising administering to the subject the vaccine vector of claim 1 in an amount effective to reduce the morbidity associated with subsequent infection of the subject with an apicomplexan parasite as compared to a control subject not administered the vaccine vector.

16. The method of claim 13, wherein the vaccine vector is administered by a route selected from the group consisting of oral, mucosal, parenteral, sub-cutaneous, intramuscular, intraocular and in ovo.

17. The method of claim 13, wherein the subject is a member of a poultry species or a mammal.

18. The method of claim 13, wherein from about $10^4$ to about $10^9$ vector copies of the vaccine are administered to the subject.

19. The method of claim 13, wherein the vaccine vector is killed prior to administration to the subject or is not capable of replicating in the subject.

20. The method of claim 16, wherein the apicomplexan parasite is selected from the group consisting of *Eimeria, Plasmodium, Toxoplasma, Neospora* and *Cryptosporidium.*

* * * * *